(12) United States Patent
Meruelo et al.

(10) Patent No.: US 10,010,628 B2
(45) Date of Patent: Jul. 3, 2018

(54) METHOD FOR INDUCING ANTITUMOR IMMUNITY USING SINDBIS VIRAL VECTORS AND TUMOR ASSOCIATED ANTIGENS

(71) Applicant: New York University, New York, NY (US)

(72) Inventors: Daniel Meruelo, Scarborough, NY (US); Tomer Granot, Brooklyn, NY (US); Yoshihide Yamanashi, Brooklyn, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/478,783

(22) Filed: Sep. 5, 2014

(65) Prior Publication Data

US 2015/0071882 A1 Mar. 12, 2015

Related U.S. Application Data

(60) Provisional application No. 61/874,685, filed on Sep. 6, 2013.

(51) Int. Cl.
*A61K 48/00* (2006.01)
*A61K 39/00* (2006.01)

(52) U.S. Cl.
CPC ...... *A61K 48/0058* (2013.01); *A61K 39/0011* (2013.01); *A61K 2039/5256* (2013.01); *A61K 2039/572* (2013.01); *C12N 2770/36143* (2013.01)

(58) Field of Classification Search
None
See application file for complete search history.

(56) References Cited

U.S. PATENT DOCUMENTS

| | | | |
|---|---|---|---|
| 7,807,147 B2 | 10/2010 | Meruelo | |
| 2004/0028693 A1 | 2/2004 | Wu et al. | |
| 2004/0102410 A1* | 5/2004 | Meruelo | A61K 31/70 514/44 R |
| 2007/0212739 A1 | 9/2007 | Mcarthur et al. | |
| 2008/0014222 A1 | 1/2008 | Simmons et al. | |
| 2014/0294765 A1* | 10/2014 | Cojocaru | C07K 16/28 424/85.2 |

OTHER PUBLICATIONS

Tseng et al.,In Vivo Antitumor Activity of Sindbis Viral VectorsJournal of the National Cancer Institute, vol. 94, No. 23, Dec. 4, 2002 pp. 1792-1802.*
Oncolytic virus—Wikipedia, downloaded Feb. 3, 2017.*
Vanderlugt et al., Epitope Spreading in Immunemediated Diseases: Implications for Immunotherapy Vanderlugt, Carol L; Miller, Stephen D. Nature Reviews.Immunology; London2.2 (Feb. 2002): 85-95.*
Webster's Seventh New Collegiate Dictionary, G. C. Merriam Co. the definition of parenteral (downloaded on May 4, 2016).*
Chen et al., A testicular antigen aberrantly expressed in human cancers detected by autologous antibody screening vol. 94, pp. 1914-1918, Mar. 1997 Proc. Natl. Acad. Sci. USA.*
Beauchemin, et al., Isolation and characterization of full-length functional cDNA clones for human carcinoembryonic antigen Molecular and Cellular Biology, Sep. 1987, p. 3221-3230.*
Diaz et al Oncolytic Immunovirotherapy for Melanoma Using Vesicular Stomatitis Virus 2840-2848, 2007.*
International Search Report and Written Opinion in International Application No. PCT/US14/54356, dated Jan. 16, 2015, 9 pages.
Russell, SJ, Peng, KW, and Bell, JC. Oncolytic virotherapy. Nat Biotechnol 30: 658-670.
Liu, TC, Galanis, E, and Kim, D (2007). Clinical trial results with oncolytic virotherapy: a century of promise, a decade of progress. Nat Clin Pract Oncol 4: 101-117.
Wein, LM, Wu, JT, and Kim, DH (2003). Validation and analysis of a mathematical model of a replication-competent oncolytic virus for cancer treatment: implications for virus design and delivery. Cancer Res 63: 1317-1324.
Vaha-Koskela, MJ, et al. Resistance to two heterologous neurotropic oncolytic viruses, Semliki Forest virus and vaccinia virus, in experimental glioma. J Virol 87: 2363-2366.
Vaha-Koskela, MJ, Heikkila, JE, and Hinkkanen, AE (2007). Oncolytic viruses in cancer therapy. Cancer Lett 254: 178-216.
Wildner, O, Blaese, RM, and Morris, JC (1999). Therapy of colon cancer with oncolytic adenovirus is enhanced by the addition of herpes simplex virus-thymidine kinase. Cancer Res 59: 410-413.
Hermiston, TW, and Kuhn, I (2002). Armed therapeutic viruses: strategies and challenges to arming oncolytic viruses with therapeutic genes. Cancer Gene Ther 9: 1022-1035.
Prestwich, RJ, et al. (2009). The case of oncolytic viruses versus the immune system: waiting on the judgment of Solomon. Hum Gene Ther 20: 1119-1132.
Kawakami, Y, et al. (1994). Cloning of the gene coding for a shared human melanoma antigen recognized by autologous T cells infiltrating into tumor. Proc Natl Acad Sci U S A 91: 3515-3519.
Lee, PP, et al (1999). Characterization of circulating T cells specific for tumor-associated antigens in melanoma patients. Nat Med 5: 677-685.
Cheever, MA, et al. (2009). The prioritization of cancer antigens: a national cancer institute pilot project for the acceleration of translational research. Clin Cancer Res 15: 5323-5337.
Fourcade, J, et al. CD8(+) T cells specific for tumor antigens can be rendered dysfunctional by the tumor microenvironment through upregulation of the inhibitory receptors BTLA and PD-1. Cancer Res 72: 887-896.
Strauss, JH, and Strauss, EG (1994). The alphaviruses: gene expression, replication, and evolution. Microbiol Rev 58: 491-562.
Tseng, JC, et al. (2004). Systemic tumor targeting and killing by Sindbis viral vectors. Nat Biotechnol 22: 70-77.

(Continued)

*Primary Examiner* — Maria G Leavitt
(74) *Attorney, Agent, or Firm* — Fish & Richardson P.C.

(57) ABSTRACT

The subject application is directed to a method for treating a mammal harboring a tumor comprising identifying a tumor associated antigen (TAA) expressed by the tumor and parenterally administering to the mammal a therapeutically effective amount of a Sindbis viral vector carrying a gene encoding the TAA to the mammal sufficient to elicit an immune response directed against the tumor, and thereby treating the tumor.

10 Claims, 19 Drawing Sheets

(56) References Cited

OTHER PUBLICATIONS

Tsuji, M, et al. (1998). Recombinant Sindbis viruses expressing a cytotoxic T-lymphocyte epitope of a malaria parasite or of influenza virus elicit protection against the corresponding pathogen in mice. J Virol 72: 6907-6910.
Tseng, JC, et al. (2004). Using sindbis viral vectors for specific detection and suppression of advanced ovarian cancer in animal models. Cancer Res 64: 6684-6692.
Granot, T, Venticinque, L, Tseng, JC, and Meruelo, D. Activation of cytotoxic and regulatory functions of NK cells by Sindbis viral vectors. PLoS One 6: e20598.
Huang, PY, Guo, JH, and Hwang, LH. Oncolytic Sindbis virus targets tumors defective in the interferon response and induces significant bystander antitumor immunity in vivo. Mol Ther 20: 298-305.
Bredenbeek, PJ, Frolov, I, Rice, CM, and Schlesinger, S (1993). Sindbis virus expression vectors: packaging of RNA replicons by using defective helper RNAs. J Virol 67: 6439-6446.
Alexopoulou, L, Holt, AC, Medzhitov, R, and Flavell, RA (2001). Recognition of double-stranded RNA and activation of NF-kappaB by Toll-like receptor 3. Nature 413: 732-738.
Leitner, WW, et al. (2003). Alphavirus-based DNA vaccine breaks immunological tolerance by activating innate antiviral pathways. Nat Med 9: 33-39.
Doyle, TC, Burns, SM, and Contag, CH (2004). In vivo bioluminescence imaging for integrated studies of infection. Cell Microbiol 6: 303-317.
Corbiere, V, et al. Antigen spreading contributes to MAGE vaccination-induced regression of melanoma metastases. Cancer Res 71: 1253-1262.
Lopes Cardozo, AM, et al. (2001). Metastatic pattern of CC531 colon carcinoma cells in the abdominal cavity: an experimental model of peritoneal carcinomatosis in rats. Eur J Surg Oncol 27: 359-363.
Tilney, NL (1971). Patterns of lymphatic drainage in the adult laboratory rat. J Anat 109: 369-383.
Hsu, KM, Pratt, JR, Akers, WJ, Achilefu, SI, and Yokoyama, WM (2009). Murine cytomegalovirus displays selective infection of cells within hours after systemic administration. J Gen Virol 90: 33-43.
Geissmann, F, Jung, S, and Littman, DR (2003). Blood monocytes consist of two principal subsets with distinct migratory properties. Immunity 19: 71-82.
Diefenbach, A, Jamieson, AM, Liu, SD, Shastri, N, and Raulet, DH (2000). Ligands for the murine NKG2D receptor: expression by tumor cells and activation of NK cells and macrophages. Nat Immunol 1: 119-126.
Arbones, ML, et al. (1994). Lymphocyte homing and leukocyte rolling and migration are impaired in L-selectin-deficient mice. Immunity 1: 247-260.
Vanderlugt, CL, and Miller, SD (2002). Epitope spreading in immune-mediated diseases: implications for immunotherapy. Nat Rev Immunol 2: 85-95.
Gardner, JP, et al. (2000). Infection of human dendritic cells by a sindbis virus replicon vector is determined by a single amino acid substitution in the E2 glycoprotein. J Virol 74: 11849-11857.
Kreiter, S, et al. Intranodal vaccination with naked antigen-encoding RNA elicits potent prophylactic and therapeutic antitumoral immunity. Cancer Res 70: 9031-9040.
Galanis, E, et al. Phase I trial of intraperitoneal administration of an oncolytic measles virus strain engineered to express carcinoembryonic antigen for recurrent ovarian cancer. Cancer Res 70: 875-882.
Norbury, CC, Malide, D, Gibbs, JS, Bennink, JR, and Yewdell, JW (2002). Visualizing priming of virus-specific CD8+ T cells by infected dendritic cells in vivo. Nat Immunol 3: 265-271.
Duwe, BV, Sterman, DH, and Musani, AI (2005). Tumors of the mediastinum. Chest 128: 2893-2909.
Khong, HT, and Restifo, NP (2002). Natural selection of tumor variants in the generation of "tumor escape" phenotypes. Nat Immunol 3: 999-1005.
Vergati, M, Intrivici, C, Huen, NY, Schlom, J, and Tsang, KY. Strategies for cancer vaccine development. J Biomed Biotechnol 2010.
Carmichael, MG, et al. Results of the first phase 1 clinical trial of the HER-2/neu peptide (GP2) vaccine in disease-free breast cancer patients: United States Military Cancer Institute Clinical Trials Group Study I-04. Cancer 116: 292-301.
Leitner, WW, Ying, H, Driver, DA, Dubensky, TW, and Restifo, NP (2000). Enhancement of tumor-specific immune response with plasmid DNA replicon vectors. Cancer Res 60: 51-55.
Cheng, WF, et al. (2002). Cancer immunotherapy using Sindbis virus replicon particles encoding a VP22-antigen fusion. Hum Gene Ther 13: 553-568.
Gavin, MA, Gilbert, MJ, Riddell, SR, Greenberg, PD, and Bevan, MJ (1993). Alkali hydrolysis of recombinant proteins allows for the rapid identification of class I MHC-restricted CTL epitopes. J Immunol 151: 3971-3980.
Huang, AY, et al. (1996). The immunodominant major histocompatibility complex class I-restricted antigen of a murine colon tumor derives from an endogenous retroviral gene product. Proc Natl Acad Sci USA 93: 9730-9735.
Restifo, NP, et al. (1995). Antigen processing in vivo and the elicitation of primary CTL responses. J Immunol 154: 4414-4422.
Tumor-Associated Antigens, Edited by Olivier Gires & Barbara Seliger, Chapter 1 by Annette Paschen: T Cell Antigens in Cancer, 2009, p. 3-22.
Mary L. Disis, Immunologic Biomarkers As Correlates of Clinical Response to Cancer Immunotherapy, Cancel Immunol Immunother, 2011, 60:433-442.
Supplementary European Search Report dated Mar. 3, 2017 in corresponding European Application No. 14841763.7.
Palmowski, Michael et al: "Intravenous injection of a lentiviral vector encoding NY-ES0-1 induces an effective CTL response.", Journal of Immunology, vol. 172, No. 3, Feb. 1, 2004 (Feb. 1, 2004 ), pp. 1582-1587.
Harrop, Richard et al: "Viral vectors for cancer immunotherapy", Frontiers in Bioscience, vol. 11, Jan. 2006 (Jan. 2006 ), pp. 804-817.
Granot, Tomer et al.: "Sindbis Viral Vectors Transiently Deliver Tumor-associated Antigens to Lymph Nodes and Elicit Diversified Antitumor CD8(+) T-Cell Immunity", Molecular Therapy, vol. 22, No. 1, Jan. 2014 (Jan. 2014), pp. 112-122.

* cited by examiner

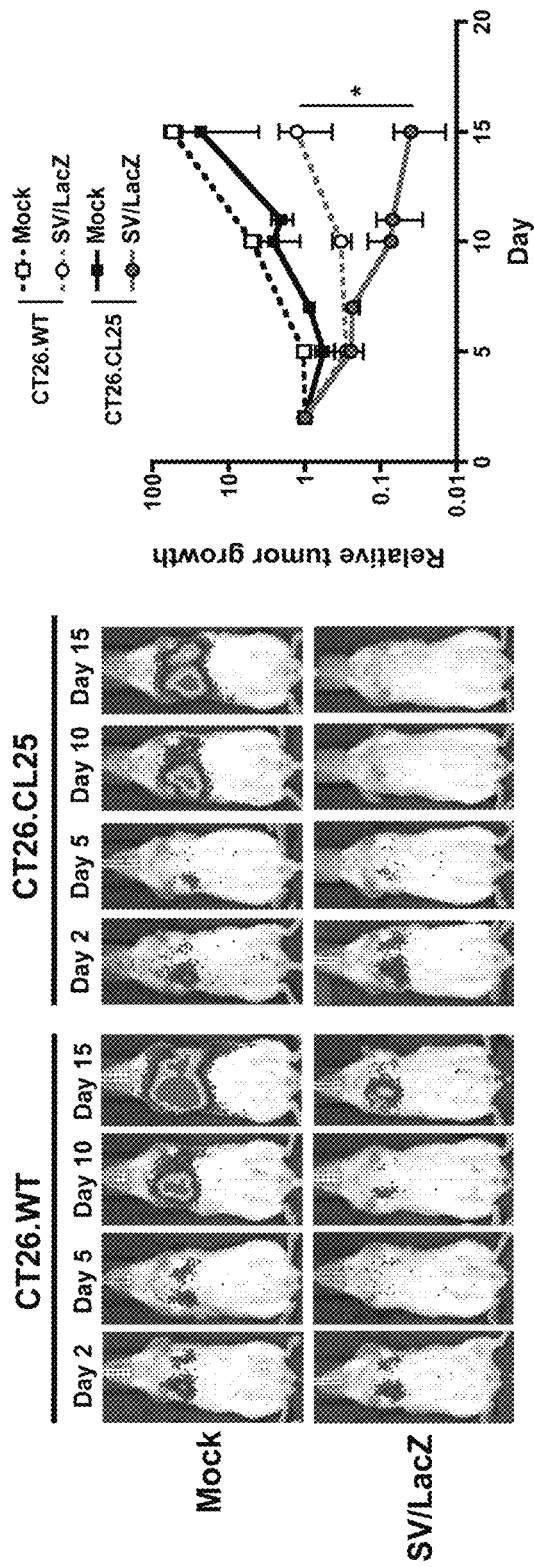
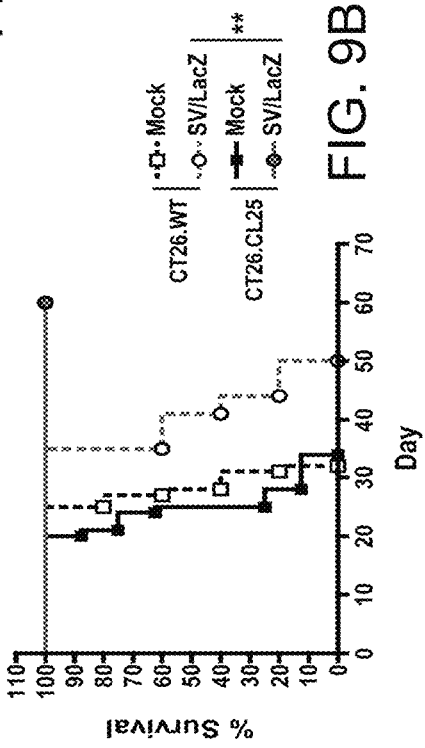
FIG. 9A
FIG. 9B

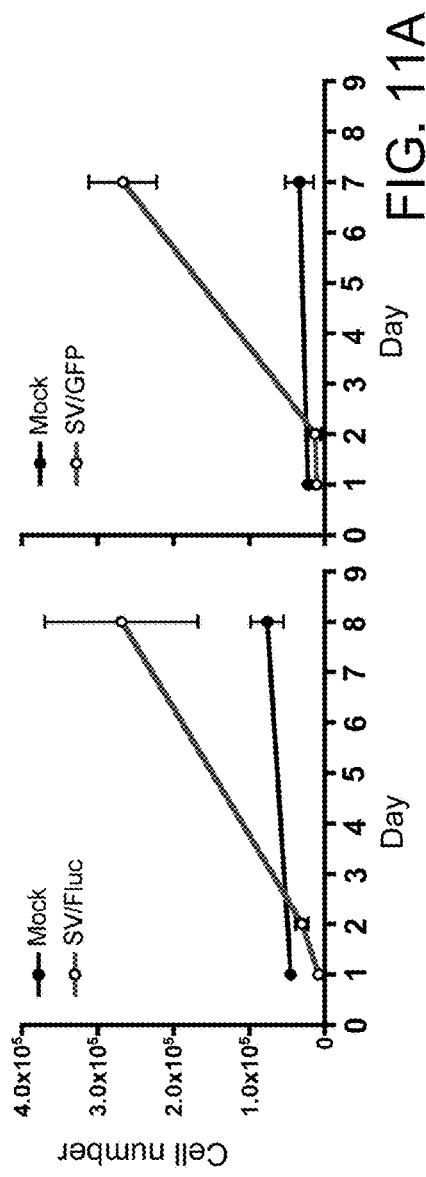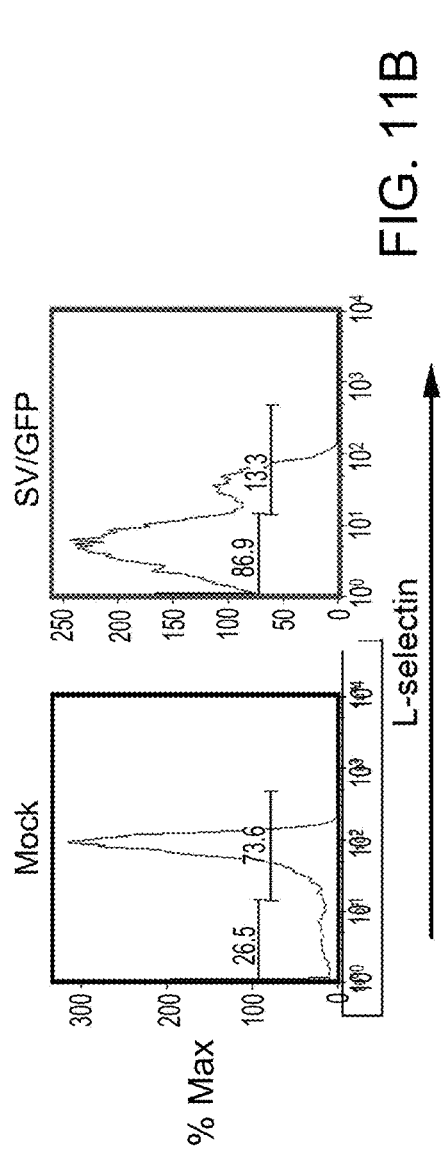
FIG. 11A
FIG. 11B

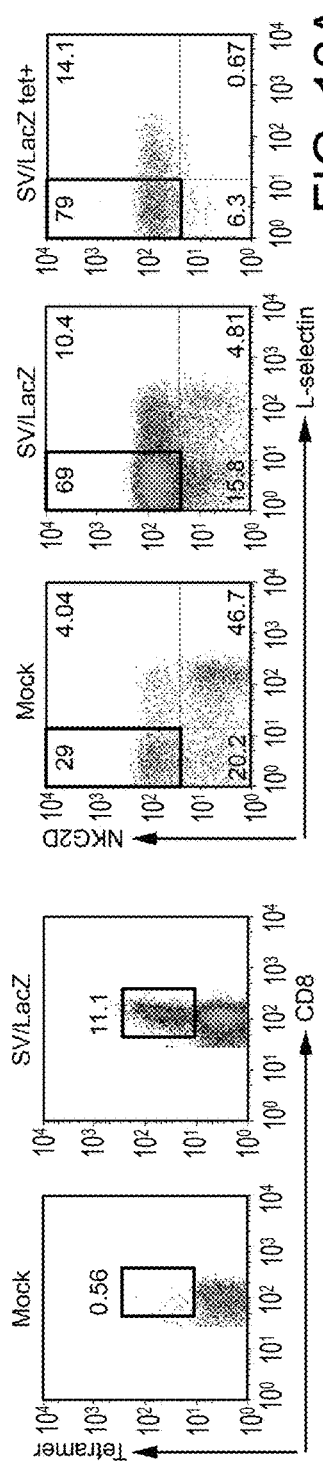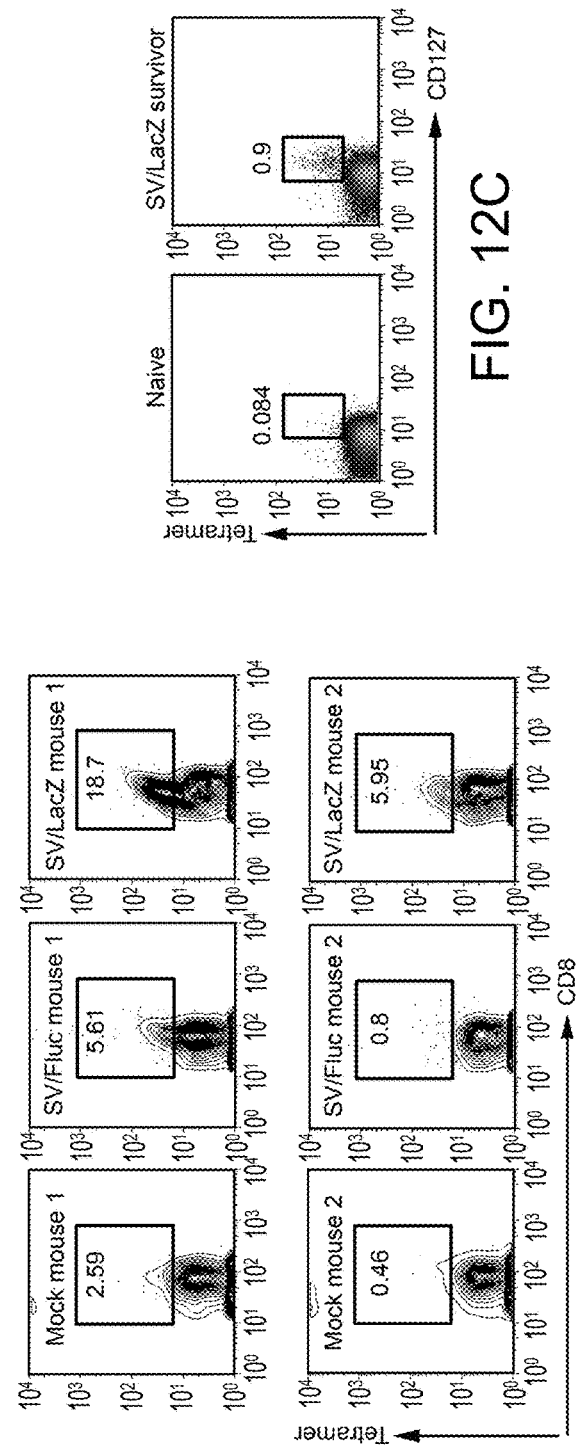
FIG. 12A
FIG. 12B
FIG. 12C

METHOD FOR INDUCING ANTITUMOR IMMUNITY USING SINDBIS VIRAL VECTORS AND TUMOR ASSOCIATED ANTIGENS

CROSS REFERENCE TO RELATED APPLICATIONS

This application is a non-provisional application of U.S. Provisional Application No. 61/874,685 filed Sep. 6, 2013, which is incorporated herein by reference in its entirety.

The United States Government has certain rights to this invention by virtue of funding received from the U.S. Public Health grants CA100687 from the National Cancer Institute, National Institutes of Health and Departments of Health and Human Services.

SEQUENCE LISTING

The instant application contains a Sequence Listing which has been submitted electronically in ASCII format and is hereby incorporated by reference in its entirety. Said ASCII copy, created on Nov. 17, 2014, is named 27522-0213001_SL.txt and is 1,057 bytes in size.

BACKGROUND OF THE INVENTION

Oncolytic viruses (OV) are viruses that specifically target and replicate in tumor cells [1]. Owing to their selectivity and oncolytic properties, OVs have generated considerable interest as an alternative or adjunct to conventional cancer therapies [2]. However, a major limitation of OV therapy is inadequate replication and propagation at the tumor site [3, 4]. Moreover, for safety reasons, many OVs are designed to be replication deficient in order to prevent them from spreading to healthy tissues, further limiting their oncolytic potential [5].

One possible solution to this problem is to supplement direct viral oncolysis with a bystander effect, in which tumor cells not directly infected by the OV will also be destroyed. This can be achieved, for example, by inserting a therapeutic or cytotoxic gene into the OV genome for delivery to the tumor site [6, 7]. Endowed with natural immunogenicity, some OVs are capable of effective stimulation of the immune system, raising the possibility of using OVs to induce an immunological anti-cancer bystander effect [8]. This idea gained further impetus with the identification [9, 10] and recent prioritization [11] of a variety of clinically relevant tumor associated antigens (TAA), which can be delivered by the OV (OV/TAA) to the tumor site [12]. In their natural state, TAAs are often poorly immunogenic [13]. However, by redirecting the anti-viral immune response towards the TAA, an immunogenic OV/TAA could potentially break this immunological tolerance. A major goal of OV research should therefore be the development of safe and effective OV/TAA agents. Sindbis virus (SV), an alphavirus with a positive single-stranded RNA genome [14], represents one of a select number of viruses that have demonstrated exceptional potential both as an OV [15, 16] and as a viral vaccine [17]. It has been previously shown that replication deficient SV vectors target and inhibit the growth of xenograft, syngeneic and spontaneous tumors in mice [16, 18].

Recently, it has also been found that SV induces the activation of natural killer (NK) cells and macrophages in tumor-bearing mice [19]. In addition, SV vectors expressing immune-modulating genes such as interleukin 12 (IL-12) have an enhanced antitumor [16] and immunostimulatory [19] effect. Nevertheless, these approaches have not generally led to complete tumor remission [19]. Moreover, some tumor cells may not be efficiently targeted by SV [20], underscoring the need to develop new ways of enhancing SV anti-cancer therapy.

Previously, it was hypothesized that the unique characteristics of SV vectors, which make them effective oncolytic agents and gene delivery systems (e.g. the ability to disseminate through the bloodstream [15] and deliver high levels of heterologous proteins [21]) could also be useful for efficient TAA delivery. Moreover, the SV life cycle, which is characterized by the absence of a DNA phase, rendering the vectors safer, also involves the production of high levels of double stranded RNA (dsRNA), a potent immunological 'danger signal' [22], and the subsequent activation of the type I interferon pathway [23]. The combination of safety, immunogenicity, efficient dissemination, and high TAA expression make SV/TAA an attractive OV/TAA candidate. Therefore, what is needed in the art are methods for treating mammals suffering from tumors using SV/TAA, thereby taking advantage of all of the above-mentioned benefits.

SUMMARY OF THE INVENTION

Disclosed herein, the BALB/c CT26 colon carcinoma tumor model was used to investigate the use of SV as an OV/TAA agent. It was found that unlike other tumor models tested, CT26 cells are not targeted by SV in vivo. Nevertheless, SV vectors carrying β galactosidase (SV/LacZ) had a remarkable therapeutic effect in mice bearing LacZ-expressing CT26 tumors. Using the in vivo imaging system (IVIS) for sensitive in vivo detection of luciferase activity [24], the mediastinal lymph nodes (MLN) were identified as a site of early transient heterologous protein expression after intraperitoneal (i.p) injection of SV vectors carrying the firefly luciferase gene (SV/Fluc). TAA delivery into the MLN marked the starting point of a potent immune response that culminated in the generation of effector and memory $CD8^+$ T cells displaying robust cytotoxicity against LacZ positive and negative tumor cells. This latter phenomenon, known as epitope spreading, has recently been suggested to be an important component of effective cancer immunotherapy in patients [25].

In one aspect, the present invention provides a method for treating a mammal harboring a tumor comprising the steps of identifying a tumor associated antigen (TAA) expressed by the tumor, and parenterally administering to the mammal a therapeutically effective amount of a Sindbis viral vector carrying a gene encoding the TAA to the mammal sufficient to elicit an immune response directed against the tumor, and thereby treating the tumor.

In another aspect, the present invention provides a method for inducing a CD8+ T-cell mediated immune response directed against a tumor in a mammal comprising the steps of identifying at least one tumor associated antigen (TAA) expressed by the tumor, and parenterally administering to a mammal in need of such treatment an amount of a Sindbis viral vector carrying a gene encoding the TAA effective to elicit a CD8+ T-cell mediated immune response directed against the tumor.

These and other aspects of the present invention will be apparent to those of ordinary skill in the art in light of the present description, claims and drawings.

BRIEF DESCRIPTION OF THE DRAWINGS

FIGS. 4a-4d. SV/LacZ induces LacZ-specific CD8$^+$ T cell response. (a,b) Splenocytes from CT26.CL25 s.c. tumor-bearing mice were collected and analyzed 2 weeks after SV/LacZ or Mock treatment started. Representative tetramer plots (a), and the percentage of tetramer-positive cells (b) are shown (N=5). (c) Cells from the peritoneal cavity of i.p. and lung tumor-bearing mice 7 days after therapy started were collected, stained and analyzed (N=4-5). (d) Lungs from lung tumor-bearing mice 7 days after treatment started were analyzed, and the percentage of activated (NKG2D high, L-selectin low) cells in the subsets of LacZ tetramer positive and negative CD8$^+$ T cells in the lungs were analyzed and plotted as in FIG. 3b (N=3). Data in (b)-(d) are expressed as mean±SEM. *$p<0.05$**$p<0.01$. SV, Sindbis viral vector.

FIGS. 9a and 9b. The enhanced therapeutic effect of SV/LacZ in mice bearing lung tumors is dependent on LacZ expression on the tumors. (a) Tumor growth was analyzed in CT26.CL25.Fluc or CT26.WT.Fluc lung tumor-bearing mice at indicated time points. The left panel shows representative IVIS images of two independent experiments. The right panel shows the relative tumor growth at indicated time points. Data are expressed as mean±SEM. (N=4-7). (b) Survival rates of CT26.CL25.Fluc or CT26.WT.Fluc lung tumor-bearing mice are shown as Kaplan-Meier survival plots (N=5-7). *p<0.05, **p<0.01. SV, Sindbis viral vector.

FIGS. 11a and 11b. SV/Fluc and SV/GFP induce CD8+ T cell response. (a) Peritoneal tumor bearing mice were treated with SV/Fluc (left panel), SV/GFP (right panel), or media (Mock). At indicated time points, peritoneal cells were analyzed using flow cytometry, and the calculated number of CD8+ T cells in the peritoneum is shown (mean±SEM, N=2-3 for each time point). (b) Representative flow cytometry plots show L-selectin expression on peritoneal CD8+ T cells from SV/GFP or mock-treated mice 7 days after treatment started (N=2). Fluc, firefly luciferase; GFP, green fluorescent protein; SV, Sindbis viral vector.

FIGS. 12a-12c. SV/TAA induces the activation of effector and memory LacZ-specific CD8+ T cells. (a) Left panel: LacZ-naïve, tumor-free mice were injected with SV/LacZ or media (Mock). Four days later, peritoneal cells were extracted and analyzed for the presence of LacZ-specific CD8+ T cells. Right panel: The activation level of peritoneal CD8+ T cells from Mock- and SV/LacZ-treated mice were compared to each other, as well as to the LacZ-specific CD8+ T cells obtained from the SV/LacZ treated mouse (SV/LacZ tet+). Activated cells were defined as NKG2D high, L-selectin low cells. (b) LacZ tetramer analysis from peritoneal CT26.CL25 tumor bearing mice treated with SV/LacZ, SV/Fluc, or media (Mock) are shown. (c) Splenocytes from naïve or SV/LacZ-treated long-term surviving mice (SV/LacZ survivor) that bore i.p. CT26.CL25 tumors were stained with anti-CD127 (memory cell marker) and LacZ specific tetramers to determine the presence of long-lasting LacZ-specific memory (CD127+, Tetramer+) cells. Data is representative of two specimens, taken more than 3 months after the treatment was stopped. All plots show gated CD8+ T cells. Fluc, firefly luciferase; LacZ, β-galactosidase; SV, Sindbis viral vector; tet, tetramer.

DETAILED DESCRIPTION OF THE INVENTION

Figure 1A:
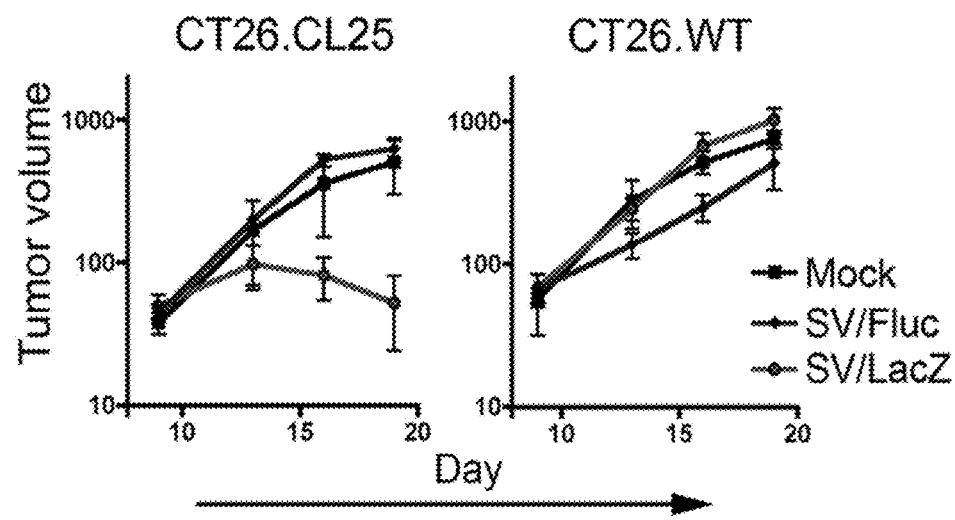
FIGS. 1a-1c. SV/LacZ inhibits the growth of LacZ-expressing CT26.CL25 tumors. (a) $0.5 \times 10^6$ LacZ-expressing CT26.CL25 (left panel) or LacZ-negative CT26.WT (right panel) cells were injected s.c. into the right flank of BALB/c mice. Starting on day 9 after tumor inoculation, mice were treated i.p. with SV/LacZ, control SV/Fluc vectors, or media (Mock). Tumor volume (mm$^3$) was measured and plotted (N=3-4). Data are representative of at least two independent experiments. (b) Kaplan-Meier survival plots of mice bearing peritoneal CT26.CL25 tumors. $2.5 \times 10^4$ CT26.CL25 cells were injected i.p., and treatment started on day 4 (N=5). Data for the SV/LacZ and mock groups is representative of 2 independent experiments. (c) Representative IVIS images of SV/LacZ and control-treated mice bearing lung CT26.CL25.Fluc tumors are shown (left panel). Relative tumor growth (top right panel) was determined by normalizing the luminescence to the first image (day 2) for each individual mouse, and survival rates were plotted (bottom right panel) (N=5-8). Data is representative of 2 independent experiments. Data in (a) and (c) are expressed as mean±SEM. *$p<0.05$**$p<0.01$. SV, Sindbis viral vector.

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

The present invention is based on the following discoveries: (i) SV represents a potentially powerful therapeutic platform for the immunogenic delivery of TAAs, (ii) the therapeutic benefit obtained from SV/TAA does not necessarily require the direct targeting of tumor cells, (iii) SV/TAA therapy involves transient early delivery of the TAA to lymph nodes draining the injection site, in particular the MLN in the case of i.p. SV injection, (iv) SV/TAA therapy induces a potent TAA-specific CD8+ T cell response, that is subsequently redirected against tumor cells expressing the cognate TAA, (v) SV/TAA therapy leads to epitope spreading, providing a possible solution to the problem of tumor escape by TAA loss or modification, and (vi) SV/TAA therapy ultimately leads to long-term survival of tumor-bearing mice, and to the generation of long-lasting memory CD8+ T cells against multiple TAAs.

Pursuant to the present invention, Sindbis viral vectors carrying genes encoding tumor associated antigens (TAAs) are used to elicit an immune response directed against tumors in mammals. Oncolytic viruses (OVs) have recently emerged as a promising strategy for the immunogenic delivery of TAAs to cancer patients. However, prior to the present invention, safe and effective OV/TAA therapies have not yet been established. It has been previously demonstrated that vectors based on Sindbis virus (SV) can target tumor cells, inhibit tumor growth and activate the innate immune system in mice. It has now been unexpectedly discovered that parenterally administered SV vectors carrying a gene encoding a tumor associated antigen (TAA) generate a dramatically enhanced therapeutic effect in mice bearing subcutaneous, intraperitoneal, and lung cancers. Surprisingly, SV/TAA efficacy was not dependent on tumor cell targeting, but was characterized by the transient expression of TAAs in lymph nodes draining the injection site. Early T cell activation at this site was followed by a robust influx of NKG2D expressing antigen-specific cytotoxic CD8+ T cells into the tumor site, subsequently leading to the generation of long-lasting memory T cells. Such cells conferred protection against re-challenge with TAA-positive as well as –negative tumor cells. As described herein, by combining in vivo imaging, flow cytometry, cytotoxicity/cytokine assays, and tetramer analysis, the relationship between these events has been discerned. As a result, a model for CD8+ T cell activation during SV/TAA therapy and a method to treat mammals suffering from tumors by eliciting an immune response directed against a tumor is provided.

SV/TAA can be combined with chemotherapy, as it has been previously shown that SV and chemotherapy can synergize (e.g. see U.S. patent application Ser. No. 13/133,680). This includes, but is not limited to, chemotherapy that stimulates the immune system, or that inhibits suppressor elements in the immune system, or that affects tumor cells and makes them more susceptible to T cell (or other immune cell) cytotoxicity. For example, there are certain chemotherapies that could facilitate SV/TAA therapy because they suppress immunosuppressive cells, thereby enhancing SV/TAA immunostimulation. There have also been reports in the literature suggesting that chemotherapy enhances tumor cell susceptibility to T cell mediated cytotoxicity, for example, Ramakrishnan et al. Journal of Clinical Investigation, 120(11):4141-4154, 2010.

In the method of the present invention, a patient afflicted with a tumor is examined to identify a TAA associated with the tumor. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor. leiomyosarcoma, rhabdomyosarcoma. Colon carcinoma, pancreatic cancer, breast cancer, ovarian cancer, prostate cancer, squamolls cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma. hepatoma. bile duct carcinoma, choriocarcinoma, seminoma, embryonal carcinoma. Wilms'•tumor. cervical cancer, testicular tumor, lung carcinoma. small cell lung carcinoma. Bladder carcinoma, epithelial carcinoma, glioma. astrocytoma, medulloblastoma, craniopharyngioma, ependymoma, pinealoma. hemangioblastoma. acoustic neuroma, oligodendroglioma, meningioma, melanoma, neuroblastoma, neuroglioma. and retinoblastoma.

Hematologic malignancies can also be treated according to the invention provided that the specific TAA can be identified.

Pursuant to the present invention, the tumor and the SV must express either the same TAA or a similar but not identical TAA that is immunologically cross-reactive with the TAA expressed by the SV/TAA. TAAs are well known in the art. For example, Cheevers et al. (Clin Cancer Res 15: 5323-5337, 2009) disclosed 75 representative TAAs for comparison and ranking, assembling information on the predefined criteria for the selected antigens, and ranking the antigens based on the predefined, pre-weighted criteria. Any TAA expressed by the tumor can be utilized. However, it is expected that there is wide variability between the efficacy of different TAAs, with some TAAs potentially inducing much stronger responses (immunodominant TAAs); exactly which ones are preferred can be determined using routine investigation well known to those of ordinary skill in the art.

The TAA expressed by a patient's tumor can be identified from a biopsy or from blood tests when a biopsy is not possible. Serological analysis of expression cDNA libraries (SEREX) has previously been used to identify human TAAs. Alternative methods can also be used.

After the relevant TAA has been identified, a Sindbis viral vector carrying a gene encoding the TAA is constructed using techniques well known in the art such as those described in the Materials and Methods below. The nucleotide sequences encoding the TAAs are also well known in the art and can be easily obtained from the literature. For example, the sequence of NY-ESO-1, a testicular antigen aberrantly expressed in human cancers was published in 1997 (Yao-Tseng ChenH, Matthew J. Scanlant, Ugur Sahin, Ozlem Tureci Ali O. Guret, Salam Tsangt, Barbara Williamsont, Elisabeth Stockertt, Michael Pfreundschu, and Lloyd J. Oldt PNAS 1997), whereas the Carcinoembryonic antigen sequence was published in 1987 (Isolation and characterization of full-length functional cDNA clones for human carcinoembryonic antigen. N Beauchemin, S Benchimol, D Cournoyer, A Fuks and C P Stanners, Molecular and Cellular Biology 1987.)

Any Sindbis viral vector can be used in the present invention, including replication competent (described, for example, in U.S. Pat. No. 8,282,916) and replication defective (described, for example, in U.S. Pat. Nos. 7,303,898, 7,306,792, and 8,093,021). Replication defective vectors are preferred for use in the present invention in order to prevent infection of healthy tissues.

Pursuant to the present invention, a single i.p. injection of a therapeutically effective amount of SV/TAA sufficient to infect the cells of the mediastinal lymph nodes (MLN) leads to their rapid immunogenic delivery to the MLN. Such therapeutically effective amounts broadly range between about between about 10 million and about 100 billion vector particles. Although in mice a single i.p. injection of SV/TAA is sufficient to elicit a detectable CD8+ mediated immune response directed against the tumor, other regimens may be necessary for achieving a maximal response. For example, between 1 and about 8 i.p. injections over a time period of between 1 week and many weeks, with the possibility of injecting one or more booster injections 1 or more years later, may be preferably administered for a maximum effect.

The MLN has previously been shown to drain the peritoneum [27, 28], and represents an environment in which antigens delivered by SV vectors (e.g., TAAs) can potentially be processed and presented to T cells by antigen presenting cells (APC) in the context of SV viral danger signals such as double stranded (ds) RNA [22]. One of the main functions of lymph nodes is to facilitate the induction of an adaptive immune response. Viral danger signals are components of the virus (or of infected cells) that stimulate the immune system. Double stranded RNA is such a danger signal because it is not normally found in cells, and is associated with viral infections. The MLN provides the location for the induction of a CD8+ T cell mediated immune response directed against the TAA. Consistent with this finding, the number of T cells in the MLN significantly increased 24 hours after SV/TAA treatment using LacZ as a model antigen.

It is also possible to use two (or more) different vectors, including the injection of different vectors carrying different cytokines at different time points to facilitate the induction and progression of an enhanced immune response against the TAA or TAAs.

In addition to CD8+ T cells, SV/TAA therapy can also activate additional immune (or non-immune) cells, including (but not limited to) CD4+ T cells, NK cells, macrophages, monocytes, dendritic cells, neutrophils, and other cells, as well as the humoral immune response. Epitope spreading can occur not only in CD8+ T cells, but also in CD4+ T cells. As can be seen in Example 2, tumor cell targeting is not required for effective SV/TAA therapy, suggesting that immune cell activation during SV/TAA therapy may occur far away from the tumor site (in this case the lungs), e.g. in lymph nodes that drain the SV injection site.

As shown in Example 3, using flow cytometry, it was confirmed that a large number of CD8+ T cells influx into the peritoneum 7 days after the first SV/TAA injection. These peritoneal CD8+ T cells were activated, as evidenced by the upregulation of NKG2D [30] and downregulation of lymph node homing receptor L-selectin [31]). In addition to the robust influx of activated CD8+ T cells into the peritoneum, a small number of NKG2D high, L-selectin low CD8+ T cells could also be seen in the lungs of mice bearing lung CT26.CL25 tumors that were treated with SV/TAA. It was found that a subset of the LacZ-specific CD8+ T cells generated during SV/LacZ therapy eventually develop into memory T cells. Splenocytes from SV/LacZ-treated long-term surviving mice that bore i.p. CT26.CL25 tumors were analyzed. Using LacZ tetramers in combination with the memory marker CD127, a population (roughly 1% of the CD8+ T cell splenocyte population) of LacZ-specific, CD127+ memory CD8+ T cells in these mice was identified more than 3 months after the last SV/LacZ injection. Therefore, treatment pursuant to the present invention led to the long term maintenance of antitumor activity.

Use of the methods of the present invention causes epitope spreading. One of the limitations of prior art cancer vaccine strategies has been the inherent heterogeneity and genomic instability of tumor cell populations, coupled with the selective pressure induced by the treatment, leading to tumor evasion by loss or modification of the TAA used in the vaccine [38, 39]. In this context, an important aspect of the present invention is the induction of epitope spreading, i.e. the expansion of the anti-tumor T cell response to incorporate novel TAAs that are endogenous to the tumor, but not delivered by the vector [32] during SV/TAA therapy. Clinical trials are increasingly incorporating the analysis of epitope spreading [40], and in some cases a positive correlation between the induction of epitope spreading and therapeutic efficacy has been shown [25]. As shown in Example 7, SV/TAA therapy against CT26.CL25 tumors caused epitope spreading, which led to the development of immunity against other unrelated antigen(s) expressed on the CT26 tumors.

In an alternative embodiment of the present invention, dual expression SV vectors that carry and deliver genes encoding TAAs in conjunction with genes encoding appropriate immune stimulating cytokines to create optimal conditions in the lymph node for T cell stimulation are employed. Such immune stimulating cytokines include, without limitation, IL-12 (disclosed in Cloning of cDNA for natural killer cell stimulatory factor, a heterodimeric cytokine with multiple biologic effects on T and natural killer cells. S F Wolf, P A Temple, M Kobayashi, D Young, M Dicig, L Lowe, R Dzialo, L Fitz, C Ferenz and R M Hewick the Journal of Immunology), and CCL17 (Molecular Cloning of a Novel T Cell-directed CC Chemokine Expressed in Thymus by Signal Sequence Trap Using Epstein-Barr Virus Vector*-Toshio Imail, Tetsuya Yoshida, Masataka Baba, Miyuki Nishimura, Mayumi Kakizaki and Osamu Yoshie. The Journal of biological Chemistry).

Additional immune stimulating cytokines include, but are not limited to: IL-1, IL-2, IL-3, IL-4, IL-5, IL-6 IL-7, IL-8, IL-9, IL-10, IL-11, IL-12, IL-13, IL-14, IL-15, IL-16, IL-17. Additional cytokines include IL-18-IL-36. In addition to CCL17, other chemokines can also be used, including, but not limited to, CCL1-CCL27 and other CC chemokines, CXCL1-CXCL13 and other CXC chemokines, C chemokines, and $CX_3C$ chemkines. Cytokine or chemokine receptors and soluble receptors can also be used. Additional immune modulators that can be used include TGF-β and TNFα. In addition, different combinations of the above-mentioned (or alternative) cytokines can be used.

Moreover, because MLN TAA expression is both transient and re-inducible (unpublished results), different cytokines can be delivered at different stages of SV/TAA therapy to further tailor the anti-tumor immune response. For example, SV/IL12 can be delivered in the early stages of SV/TAA therapy in order to stimulate a Th1 cytotoxic T cell response, and SV/CCL17 can be delivered later on, in order to enhance the cross-priming of additional TAAs, thereby increasing epitope spreading.

It has been previously demonstrated that SV vectors carrying the IL-12 gene have an enhanced therapeutic effect in tumor-bearing mice [16], and promote the IFN-γ-dependent activation of M1 type macrophages [19]. However, the effects of IL-12 delivery to the MLN have not specifically been investigated before the present invention.

In another alternative embodiment, SV vectors are used to target and/or to deliver payloads to mediastinal masses such as those derived from certain neurogenic tumors [37]. Since tumors often metastasize to the lymph nodes (including the mediastinal lymph nodes), and SV can naturally target certain lymph nodes (including the mediastinal lymph nodes), SV can be used to deliver antigens, cytokines, or other payloads directly to the site of tumor growth.

Multiple TAAs can also be used either by using one Sindbis vector expressing multiple TAAs, or by using multiple Sindbis vectors expressing different TAAs. In addition, the route of administration is parenteral, including, but not limited to, intravenous, intraperitoneal, subcutaneous, intramuscular, intranasal, intraorbital, intranodular, and intratumoral injections.

The model for the method is presented below:

Step 1: i.p. injection of SV/TAA results in transient immunogenic expression of TAA in the mediastinal lymph nodes, followed by the induction of T cell activation at this site and/or in alternative locations; NK cells are also activated against the tumor cells. Step 2 TAA-specific CD8+ T cell cytotoxicity results in the destruction of tumor cells and the subsequent release of tumor associated antigens. Step 3: Antigen-presenting cells capture and present these antigens to CD8+ T cells in the tumor-draining lymph nodes, resulting in epitope spreading, including the induction of TAA-specific CD8+ T cells that can potentially target TAA(−) tumor cell escape variants. Step 4: memory CD8+ T cells against a variety of tumor-associated antigens are generated.

The present invention is described further below in working examples which are intended to further describe the present invention without limiting the scope thereof.

Materials and Methods

Cell Lines.

Baby hamster kidney (BHK), CT26.WT, and LacZ-expressing CT26.CL25 cells were obtained from the American Type Culture Collection. Firefly luciferase (Fluc)-expressing CT26 cells (CT26.WT.Fluc and CT26.CL25.Fluc) for non-invasive bioluminescent imaging were generated by stable transfection of a Fluc-expressing plasmid into CT26.WT and CT26.CL25 cells. The Fluc-expressing plasmid was constructed by introducing a SV40 promoter sequence into the multi-cloning site of pGL4.20 vector (Promega, WI).

Cell Culture.

BHK cells were maintained in minimum essential a-modified media (a-MEM) (Mediatech, VA) with 10% fetal bovine serum (FBS) (Atlanta Biologicals, Norcross, Ga.). CT26.WT, CT26.CL25, CT26.WT.Fluc, and CT26.CL25.Fluc cells were maintained in Dulbecco modified essential media (DMEM) containing 4.5 g/L glucose (Mediatech) supplemented with 10% FBS. All basal media were supplemented with 100 mg/mL of penicillin-streptomycin (Mediatech) and 0.5 mg/mL of amphotericin B (Mediatech). For culturing CT26.CL25 and CT26.CL25.Fluc cells, 0.4 mg/ml of G418 sulfate (Mediatech) was added to the basal media. For culturing CT26.WT.Fluc and CT26.CL25.Fluc cells, 5 mg/ml of puromycin (Sigma-Aldrich, MO) was added to the basal media.

SV/TAA Production.

SV/LacZ was used as an immunogenic SV/TAA agent, and SV/Fluc and SV/GFP were used as control vectors. SV/Fluc was also used for imaging experiments (see below). Vectors were produced as previously described [16]. Briefly, plasmids carrying the replicon (SinRep5-LacZ, SinRep5-GFP or SinRep5-Fluc) or DHBB helper RNAs (SinRep5-tBB) were linearized with XhoI (for SinRep5-LacZ, Sin-Rep5-GFP and SinRep5-tBB) or PacI (for SinRep5-Fluc). In vitro transcription was performed using the mMessage mMachine RNA transcription kit (Ambion, Tex.). Helper and replicon RNAs were then electroporated into BHK cells and incubated at 37° C. in—MEM supplemented with 10% FBS. After 12 hours, the media was replaced with OPTI-MEM I (Invitrogen, CA) supplemented with $CaCl_2$ (100 g/mL) and cells were incubated at 37° C. After 24 hours, the supernatant was collected, centrifuged to remove cellular debris, and frozen at −80° C. Titers of the vectors were determined as previously described [15].

Mice and Tumor Inoculation.

4-8-week-old female BALB/c mice were purchased from Taconic (Germantown, N.Y.). For the s.c. tumor model, $0.5 \times 10^6$ or $1 \times 10^6$ CT26.WT or CT26.CL25 cells in 0.2 mL PBS were injected s.c. into the right flank of each mouse. For the i.p. tumor model, $2.5 \times 10^4$ or $5 \times 10^4$ CT26.CL25 cells in 0.2 mL PBS were injected i.p. into each mouse. For the lung tumor model, $0.3 \times 10^6$ CT26.WT.Fluc or CT26.CL25.Fluc cells in 0.2 ml PBS were injected i.v. into each mouse.

Therapeutic Efficacy.

In the s.c. tumor model, treatment started after tumor volume was more than 40 mm$^3$ (volume=width×width× length/2). In the i.p. tumor model, treatment started on day 4 after tumor cell inoculation. In the lung tumor model, treatment started on day 3 after tumor cell inoculation. SV/LacZ, SV/GFP or SV/Fluc (~$10^7$ plaque forming units in 0.5 mL of OPTI-MEM I) and mock treatments (0.5 mL of OPTI-MEM I supplemented with 100 mg/L $CaCl_2$) were administered i.p. 4 times a week for 2 weeks, for a total of 8 treatments. Therapeutic efficacy was monitored in three ways: tumor volume (for s.c. tumors, measured with mechanical calipers), tumor luminescence (for lung tumors), and survival (for i.p. and lung tumors). Noninvasive bioluminescent imaging was done using the IVIS Spectrum imaging system (Caliper Life Sciences, Inc., MA), and tumor growth was quantified using the Living Image 3.0 software (Caliper Life Sciences) as previously described [16]. Survival was monitored and recorded daily.

Bioluminescent Imaging of SV/Fluc.

Tumor-bearing and tumor-free mice were injected with SV/Fluc (~$10^7$ plaque forming units in 0.5 mL of OPTI-MEM I 0.5 ml) intraperitoneally. After the treatment, bioluminescence signal was detected by IVIS at the indicated time points as previously described [16].

Ex Vivo Cytotoxicity Assay.

Lung lymphocytes or splenocytes from tumor-bearing mice were collected 7 days after SV treatment started. Lung lymphocytes ($1 \times 10^5$/ml) or splenocytes ($2 \times 10^6$/ml) were co-cultured with CT26.WT.Fluc cells ($2 \times 10^4$/ml) or CT26.CL25.Fluc cells ($2 \times 10^4$/ml) in a 24-well plate for 2 days in 1 ml RPMI 1640 supplemented with 10% FBS. Culture media were then collected for interferon (IFN)-γ secretion assays, and the remaining cells in each well were washed twice with PBS. Cells were then lysed with 100 µl of M-PER Mammalian Protein Extraction Reagent (Pierce, Ill.) per well. Cytotoxicity was assessed based on the viability of the CT26 cells, which was determined by measuring the luciferase activity in each well. Luciferase activity was analyzed by adding 100 µl of Steady-Glo reagent (Promega corp., WI) to each cell lysate, and measuring the luminescence using a GLOMAX portable luminometer (Promega corp.).

IFN-γ Secretion Assay.

Lung lymphocytes ($1 \times 10^5$/ml) or splenocytes ($2 \times 10^6$/ml) were stimulated by CT26 tumor cells ($2 \times 10^4$/ml) or immunogenic peptides (5 µg/ml) in a 24-well plate in 1 ml RPMI 1640 (Mediatech) supplemented with 10% FBS. The peptides used were the LacZ peptide TPHPARIGL (SEQ ID NO: 1) [43], the gp70 peptide SPSYVYHQF SEQ ID NO: 2) [44], or the P1A peptide LPYLGWLVF (SEQ ID NO: 3) as a negative control [45]. After stimulation, IFN-γ levels in the media were measured using a mouse IFN-γ Quantikine ELISA kit (R&D systems, Minneapolis, Minn.). TPH-PARIGL (SEQ ID NO: 1) and SPSYVYHQF SEQ ID NO: 2)-mediated increase in IFN-γ secretion was calculated by subtracting the IFN-γ levels in the control (LPYLGWLVF (SEQ ID NO: 3) stimulated) samples from the IFN-γ levels in the TPHPARIGL (SEQ ID NO: 1) and SPSYVYHQF (SEQ ID NO: 2) stimulated samples.

Flow Cytometry.

Anti-mouse antibodies anti-CD8a eFluor® 450 and eFluor® 650NC, anti-CD4 PE-Cyanine7, anti-CD69 PE, anti-CD314 (NKG2D) PE-Cyanine7, anti-CD62L (L-selectin) FITC and Alexa Fluor® 700 and anti-CD45 eFluor® 450 were purchased from eBioscience (San Diego, Calif.). PE-labeled LacZ tetramers were obtained from the NYU Vaccine and Cell Therapy Core (New York, N.Y.), and APC-labeled gp70 tetramers were obtained from the NIH Tetramer Core Facility (Atlanta, Ga.). For flow cytometry analysis of lung lymphocytes and splenocytes, mice were euthanized, and their lungs and spleens were extracted. The extracted lungs were chopped into small pieces and incubated with a digestion mix (collagenase I (50 µg/ml), collagenase IV (50 µg/ml), hyaluronidase V (25 µg/ml) and DNAse I (20 units/ml)) for 30 minutes at 37° C. Extracted spleens and digested lungs were then mashed through 70-100 µm cell strainers, followed by a treatment with 1×RBC lysis buffer (eBioscience) to eliminate red blood cells. Peritoneal cells were collected from peritoneal exudates as previously described [19]. Cells were then stained with various Abs, washed twice with HBSS (Mediatech) and analyzed using an LSR II machine (BD biosciences, CA). Data was analyzed using FlowJo (Tree Star, San Carlos, Calif.).

CD8+ T Cell Depletion.

CD8+ T cells were depleted using anti-CD8 antibody (clone 2.43) (Bio X cell, Lebanon, N.H.). 0.4 mg antibody in 0.2 mL PBS was injected into each mouse, starting 1 day before the first SV treatment, and then every 2-3 days for 2 weeks. Control mice were injected with PBS.

Statistics.

For flow cytometry, IVIS imaging, ELISA, tumor growth, and survival experiments, student t tests (2-tailed), analysis of variance (ANOVA) followed by Dunnett's test, or Kaplan-Meier log-rank test were done using Prism® 4 for Macintosh (GraphPad Software, Inc., La Jolla, Calif.).

Example 1: SV/LacZ Inhibits the Growth of LacZ-Expressing Tumors in Immunocompetent Mice In order to evaluate the use of SV vectors carrying TAAs for cancer therapy, a LacZ-expressing mouse colon cancer cell line (CT26.CL25) as a model tumor-TAA system. Initially, SV/TAA (SV/LacZ) efficacy in mice bearing subcutaneous (s.c.) tumors was tested. As seen in FIG. 1a, SV/LacZ significantly inhibited the growth of LacZ-expressing CT26.CL25 tumors, while the control vector SV/Fluc had no observable therapeutic effect (FIG. 1a, left panel). On the other hand, both SV/LacZ and SV/Fluc had little effect on the growth of LacZ-negative CT26.WT tumors (FIG. 1a, right panel). These results demonstrate that SV/LacZ has a powerful antigen-dependent therapeutic effect in mice bearing s.c. CT26 tumors.

Figure 1B:
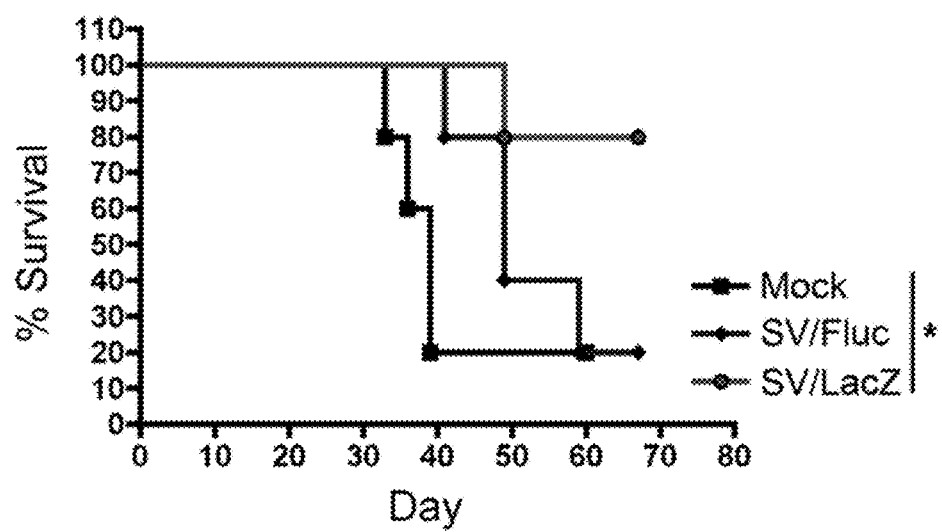
Figure 1C:
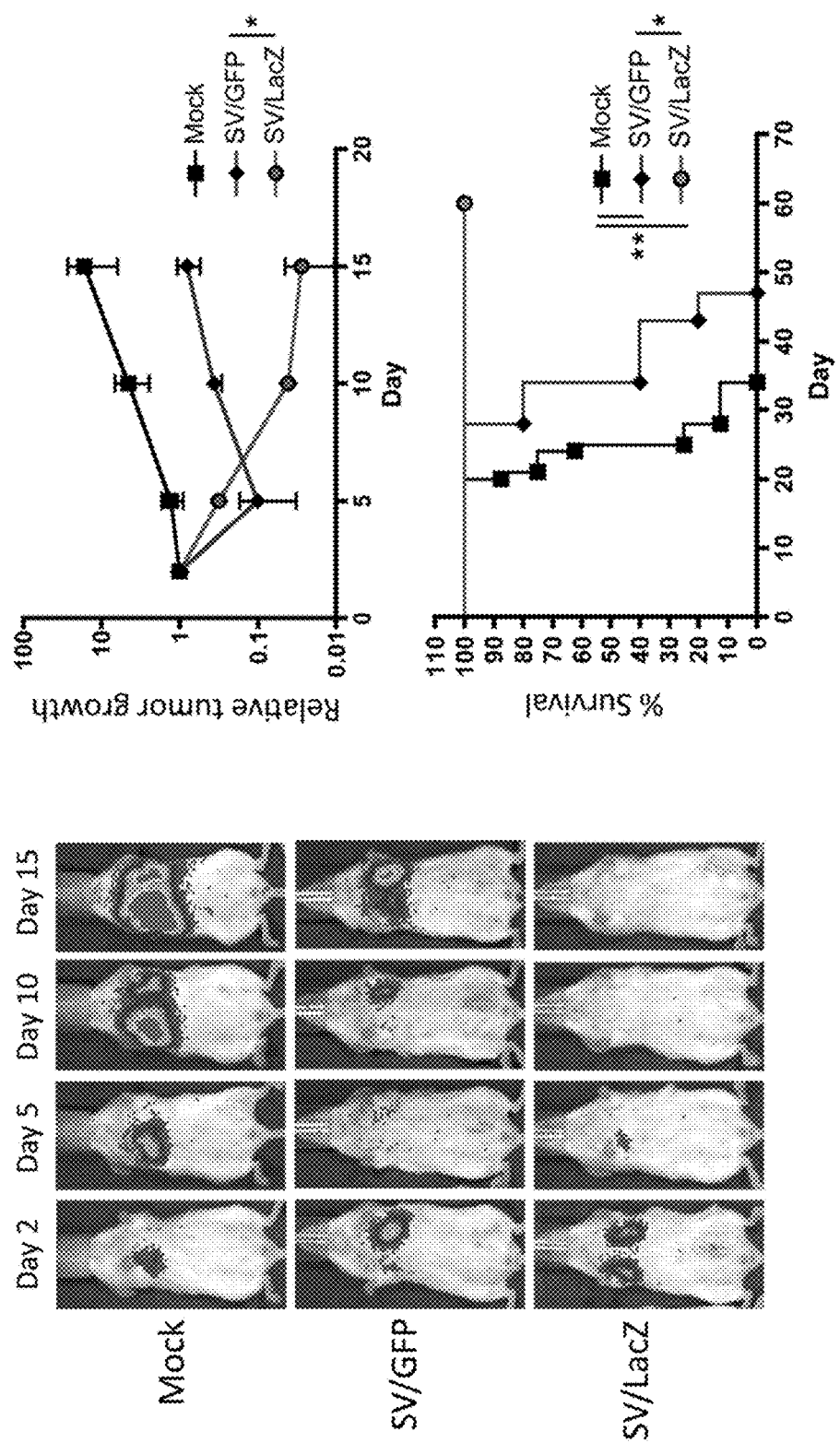

In order to investigate SV/LacZ efficacy in a physiologically relevant model of colon cancer, CT26.CL25 cells were injected intraperitoneally to mimic peritoneal carcinomatosis [26]. Therapeutic efficacy in this model was assessed by monitoring mouse survival. As in the s.c. model, SV/LacZ was found to have a potent therapeutic effect against these tumors, while the control vector (SV/Fluc) had only a minor therapeutic effect (FIG. 1b). Next, the efficacy of SV/LacZ against tumors growing in the lung was examined. To supplement the survival data in this model, Fluc-expressing CT26 cell lines (CT26.CL25.Fluc and CT26.WT.Fluc) were constructed, which can be used to monitor tumor growth noninvasively using the IVIS imaging system [16]. I.v. injection of Fluc-expressing CT26.CL25 cells produced lung tumors, and it was found that SV/LacZ induced complete tumor remission and long-term survival in this model, while the control vector, SV/GFP, only slightly delayed tumor growth and did not result in long-term survival (FIG. 1c). As in the s.c. tumor model, the enhanced therapeutic effect obtained from SV/LacZ in the lung tumor model was dependent on the expression of the TAA (LacZ) from both the vector and the tumor cells, as LacZ-negative CT26.WT tumor growth was only slightly inhibited by SV/LacZ (FIG. 9). Taken together, these results demonstrate that SV vectors carrying a TAA induce a potent therapeutic effect in mice bearing TAA-expressing CT26 tumors, regardless of the site of tumor growth.

Figure 2A:
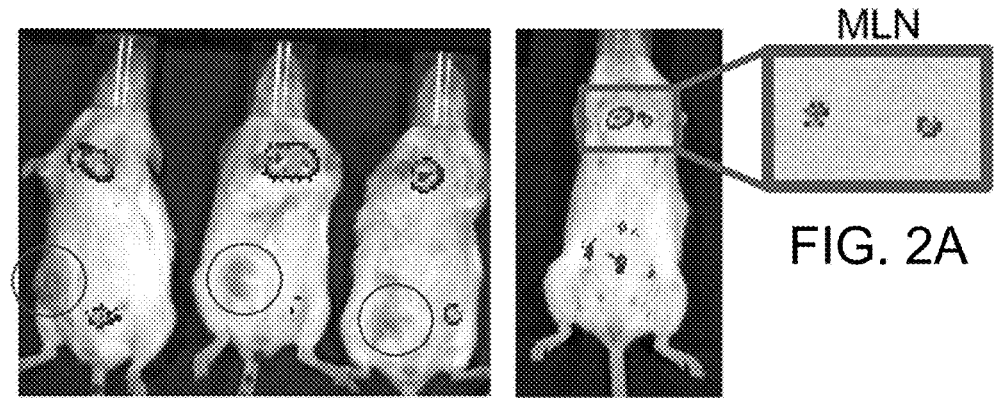
FIGS. 2a-2c. TAA expression and T cell activation occur in the mediastinal lymph nodes. (a) s.c. CT26.CL25 tumor-bearing mice (left panel) or tumor-free mice (right panel) were treated i.p. with SV/Fluc. 3 hours after the $5^{th}$ (left panel) or $1^{st}$ (right panel) treatment, bioluminescent images were taken to monitor Fluc expression from the vector. To determine the source of the upper body signal, the MLN was extracted and imaged separately (right panel). Red circles in the left panel indicate the location of the s.c. tumor in each mouse. (b) Mice bearing lung CT26.CL25.Fluc tumors were treated with SV/LacZ. 24 hours later, mediastinal and inguinal lymph nodes were extracted and stained to determine the percentage of T cells (CD3 positive, MHC class II negative) in the lymph nodes. Representative plots (left panel), and their quantification (right panel; n=3) are shown. (c) The expression of CD69 on CD8$^+$ T cells extracted from mediastinal and inguinal lymph nodes of lung tumor-bearing mice 24 hours after i.p. SV/LacZ injection was analyzed. Representative flow cytometry plots (left panel), and bar graphs showing the percentage of CD69-high cells (right panel; n=3) are shown. Data in (b) and (c) are representative of two independent experiments (the second experiment was done in mice bearing i.p. tumors), and are expressed as mean±SEM. *$p<0.05$**$p<0.01$. Fluc, firefly luciferase; MLN, mediastinal lymph node; ILN, inguinal lymph node; S/L, SV/LacZ (SV, Sindbis viral vector); TAA, tumor-associated antigen.
Figure 10B:
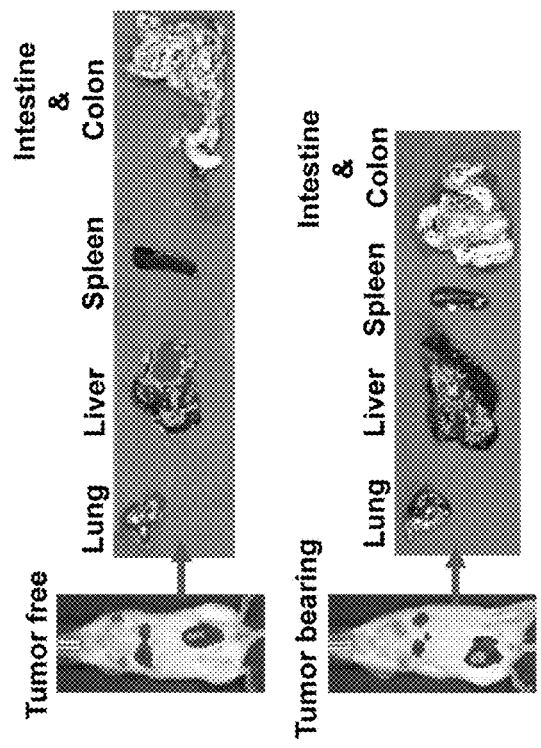
FIGS. 10a and 10b. SV does not target CT26 tumors in the lung. (a) Tumor-free or CT26.WT lung tumor-bearing mice were treated i.p. with SV/Fluc every 2 days. Whole body bioluminescent images were taken at indicated time points after the first SV/Fluc treatment. (b) On day 6, whole body images were taken, and then the indicated organs were extracted and imaged separately. Fluc, firefly luciferase; SV, Sindbis viral vector.
Figure 10A:
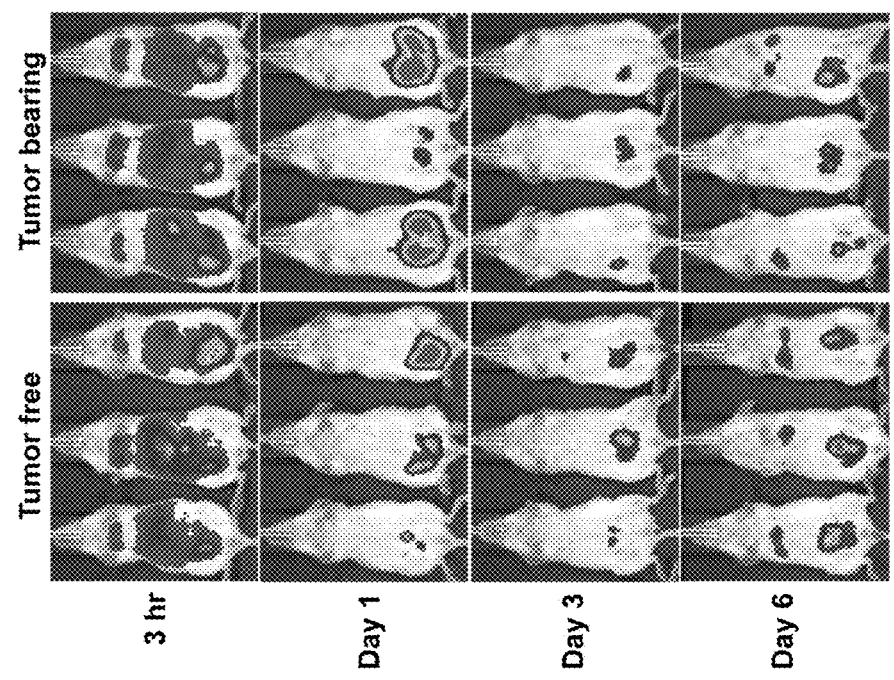

Example 2: Mediastinal Lymph Nodes Transiently Express Antigens Delivered by SV Vectors, and are a Site of Early T Cell Activation During SV Therapy It has been previously shown that SV vectors have oncolytic potential, and can target certain tumors in vivo [16]. In order to evaluate the role of tumor cell targeting in the therapeutic effect observed in the CT26 tumor model, tumor-bearing mice were treated with SV/Fluc vectors, which can be used to monitor vector localization in mice [16]. It was found that even after multiple injections, SV vectors did not target s.c. growing CT26.CL25 tumors (FIG. 2a, left panel). Similarly, the vectors did not target lung tumors; instead, SV/Fluc was seen in the peritoneal fat of tumor-bearing mice 24 hours after the first injection, and in the liver 5 days later (FIG. 10). This general pattern was not dependent on the presence of tumor cells, and occurred in tumor-free mice as well (FIG. 10). These results are consistent with other studies demonstrating that CT26 cells are not infected by SV in vitro [20], and suggest that the powerful therapeutic effect obtained from SV/LacZ is not dependent on tumor cell targeting.

Interestingly, by focusing on very early time points after SV/Fluc injection, it was noticed that a transient Fluc signal can be seen in the upper body as early as 3 hours after i.p. SV/Fluc injection (FIG. 2a and FIG. 10). By extracting the mediastinal lymph nodes (MLN) and imaging them separately, it was determined that the upper body signal originated from these lymph nodes (FIG. 2a, right panel). Notably, transient Fluc expression in the MLN occurred in both tumor-bearing and tumor-free mice (FIG. 10).

Figure 2B:
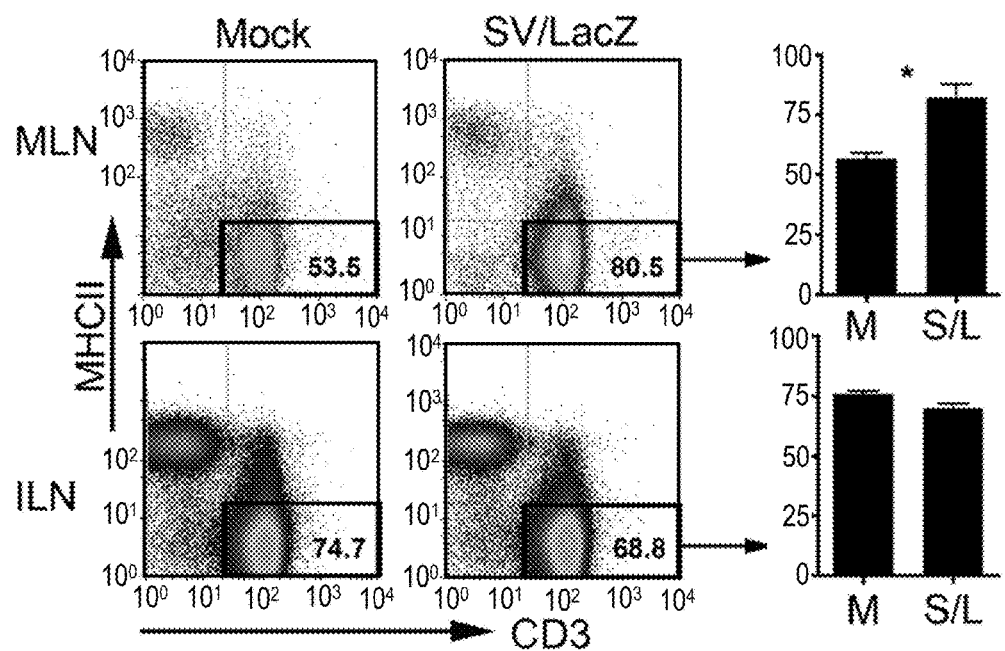
Figure 2C:
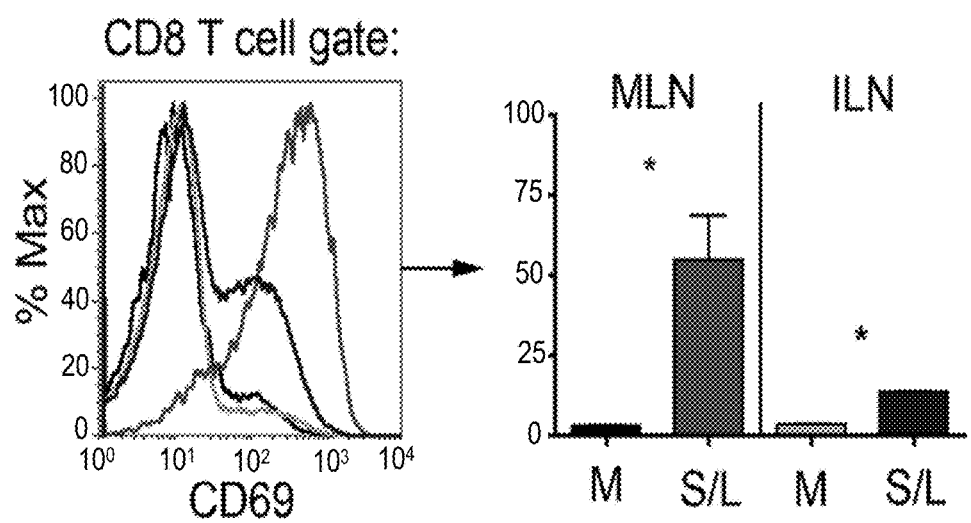

The MLN has previously been shown to drain the peritoneum [27, 28], and represents an environment in which antigens delivered by SV vectors (such as Fluc, LacZ, or other TAAs) can potentially be processed and presented to T cells by antigen presenting cells (APC) in the context of SV viral danger signals such as double stranded (ds) RNA [22]. The MLN therefore provides a possible location for the induction of an immune response to SV/TAA. Consistent with this hypothesis, the number of T cells in the MLN significantly increased 24 hours after SV/LacZ treatment (FIG. 2b). As a control lymph node, we used the inguinal lymph nodes (ILN), which do not directly drain the peritoneal cavity [29], and were not targeted by i.p. injection of SV/Fluc (FIG. 2a and additional data not shown). Unlike the MLN, there was no increase in T cells in the ILN 24 h after SV/LacZ injection (FIG. 2b). In addition to the apparent influx of T cells into the MLN, the expression of CD69, which is an early activation marker of T cells, was highly induced on CD8+ T cells in the MLN 24 hours after SV/LacZ treatment (FIG. 2c). In contrast, CD8+ T cells from the control ILN were significantly less activated, though a slight increase in CD69 expression was observed in these cells (FIG. 2c). Taken together, FIG. 2 demonstrates that tumor cell targeting is not required for effective SV/LacZ therapy, and suggests that immune cell activation during SV/LacZ therapy may occur far away from the tumor site, e.g. in lymph nodes that drain the SV injection site.

Example 3: SV/LacZ Treatment Induces a Robust Activation of CD8+ T Cells

Figure 3A:
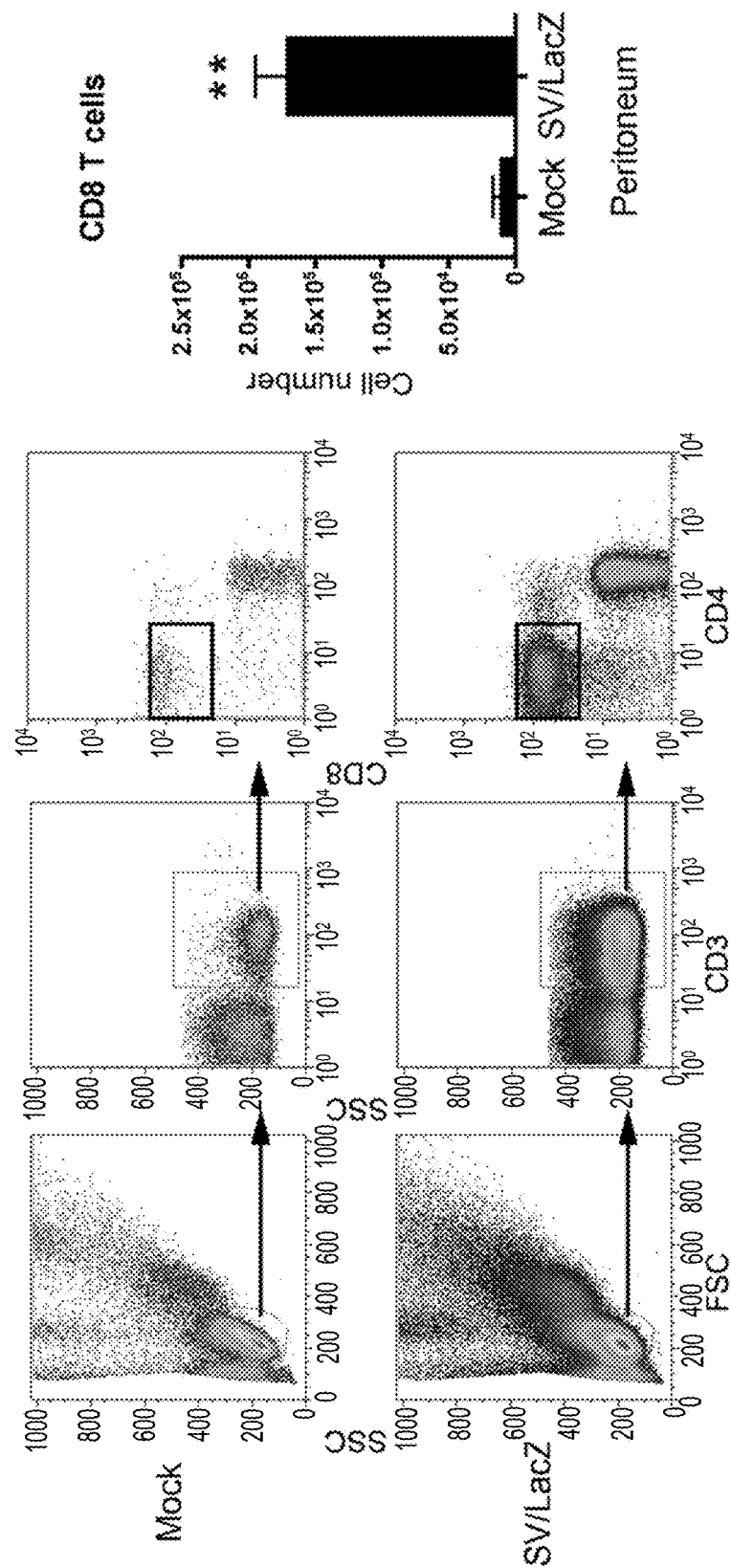
FIGS. 3a and 3b. SV/LacZ induces potent CD8$^+$ T cell response. (a) Lung CT26.CL25.Fluc tumor bearing mice were treated with SV/LacZ or media (Mock). 7 days later, peritoneal cells were analyzed. Representative flow cytometry plots (left panel), and the calculated number of CD8$^+$ T cells (right panel) are shown (mean±SEM, N=3). (b) CD8$^+$ T cells from the peritoneum and the lungs were further analyzed to determine their activation state, using NKG2D and L-selectin as activation markers. Representative flow cytometry plots (left panel) and the calculated percentage of activated (NKG2D high, L-selectin low) cells (right panel) are shown (mean±SEM, N=3). *$p<0.05$**$p<0.01$. SV, Sindbis viral vector.
Figure 3B:
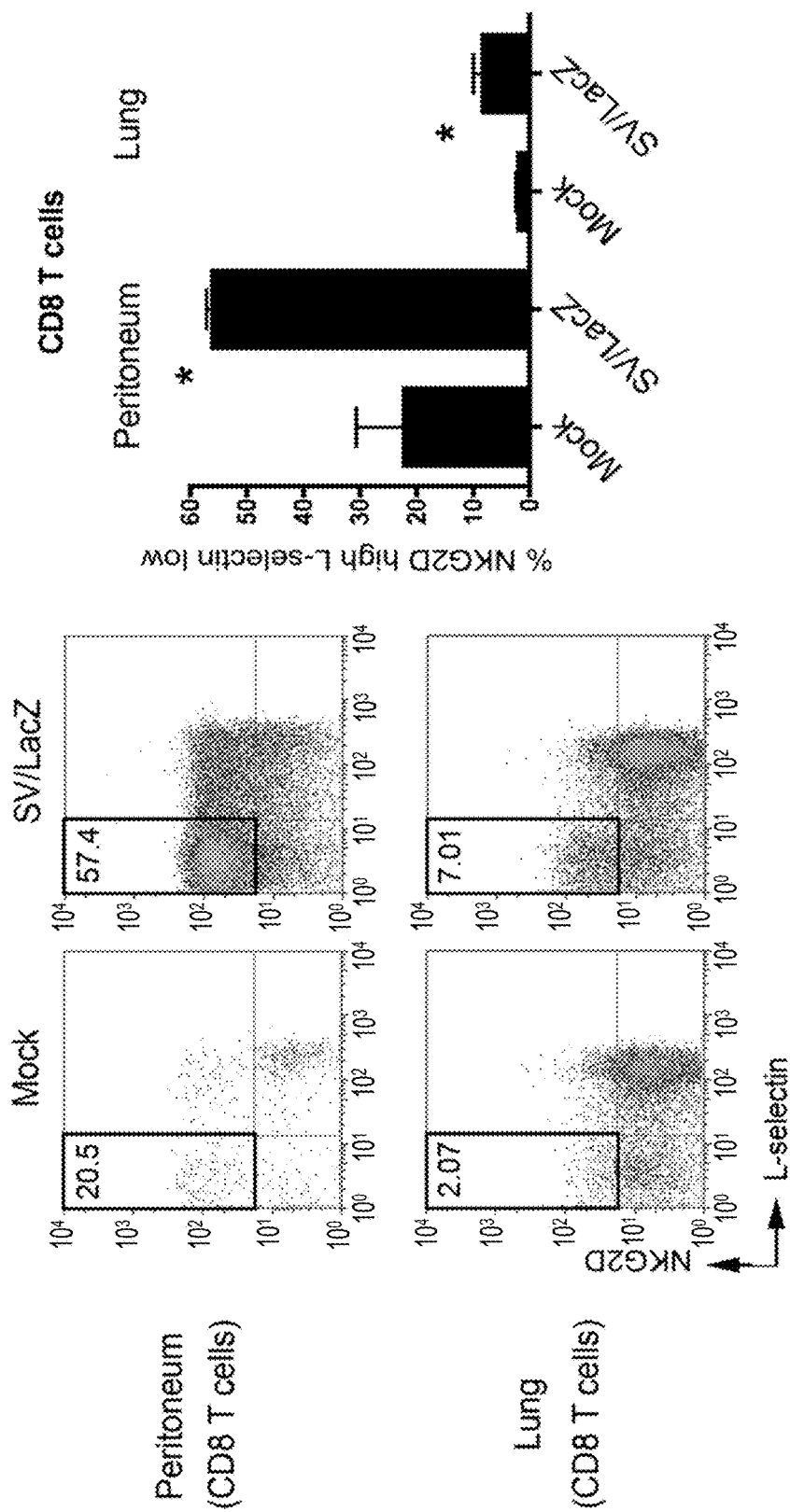

Because the activation of CD8+ T cells in lymph nodes draining the SV injection site was observed, it was anticipated that activated CD8+ T cells might subsequently migrate into the injection site in the peritoneum. Using flow cytometry, it was confirmed that a large number of CD8+ T cells influx into the peritoneum by 7 days after the first SV/LacZ injection (FIG. 3a). These peritoneal CD8+ T cells were activated, as evidenced by their upregulation of NKG2D [30] and downregulation of lymph node homing receptor L-selectin [31] (FIG. 3b). In addition to the robust influx of activated CD8+ T cells into the peritoneum, a small number of NKG2D high, L-selectin low CD8+ T cells could also be seen in the lungs of mice bearing lung CT26.CL25 tumors that were treated with SV/LacZ (FIG. 3b).

Example 4: SV/LacZ Treatment Induces LacZ-Specific Effector and Memory CD8+ T Cells The fact that SV therapeutic efficacy depends on the expression of LacZ from both the vector and the tumor cells (FIG. 1 FIG. 9), in conjunction with the robust activation of CD8+ T cells observed during SV/LacZ therapy (FIGS. 2 and 3) suggest that CD8+ T cells may be involved in the anti-cancer effect of SV/LacZ in this model. Nevertheless, CD8+ T cell activation also occurred during SV/GFP and SV/Fluc therapy (FIG. 11), even though these vectors had significantly lower therapeutic efficacy (FIG. 1). It was hypothesized that what distinguishes SV/LacZ from the other vectors is its ability to directly stimulate LacZ-specific CD8+ T cells that can subsequently target LacZ-expressing tumors. To demonstrate this concept, SV/LacZ was injected into a LacZ-naïve tumor-free mouse, a robust LacZ-specific CD8+ T cell response in the peritoneum 4 days later was observed (FIG. 12a). An increase in LacZ-specific CD8+ T cells was also observed in the spleens of s.c. tumor-bearing mice (FIGS. 4a and b), in the peritoneum of i.p. and lung tumor-bearing mice (FIG. 4c), and in the lungs of lung tumor-bearing mice (FIG. 4d, left panel) treated with SV/LacZ. Fewer LacZ-specific CD8+ T cells were seen in mice treated with control vectors (FIG. 12b). As expected, LacZ-specific CD8+ T cells from SV/LacZ-treated mice were characterized by an activated (NKG2D high, L-selectin low) phenotype (FIG. 4d, right panel, and FIG. 12a, right panel). Taken together, these results demonstrate that SV/LacZ treatment leads to the potent activation of LacZ-specific CD8+ T cells, providing a possible mechanism for the LacZ-dependent efficacy seen in FIG. 1.

In order to determine if a subset of the LacZ-specific CD8+ T cells generated during SV/LacZ therapy eventually develop into memory T cells, splenocytes from SV/LacZ-treated long-term surviving mice that bore i.p. CT26.CL25 tumors were analyzed. Using LacZ tetramers in combination with the memory marker CD127, a population (roughly 1% of the CD8+ T cell splenocyte population) of LacZ-specific, CD127+ memory CD8+ T cells in these mice was identified, more than 3 months after the last SV/LacZ injection. Control splenocytes from naïve mice had only background levels of this population (under 0.1%) (FIG. 12c).

Figure 4D:
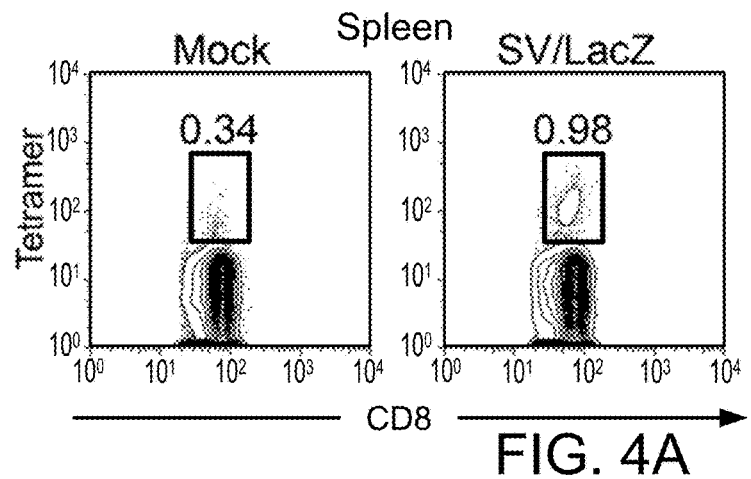
Figure 4D:
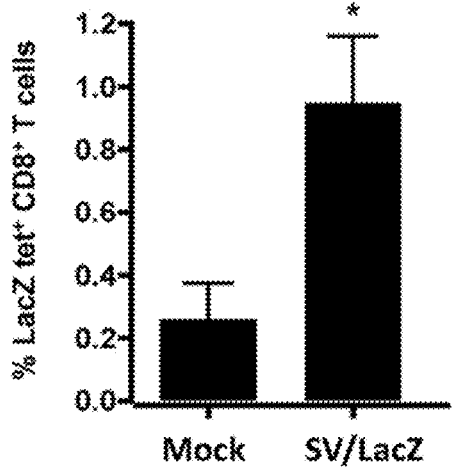
Figure 4D:
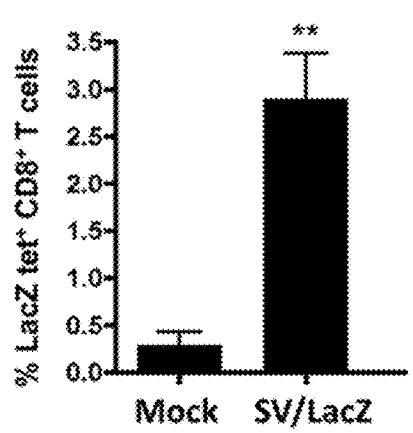
Figure 4D:
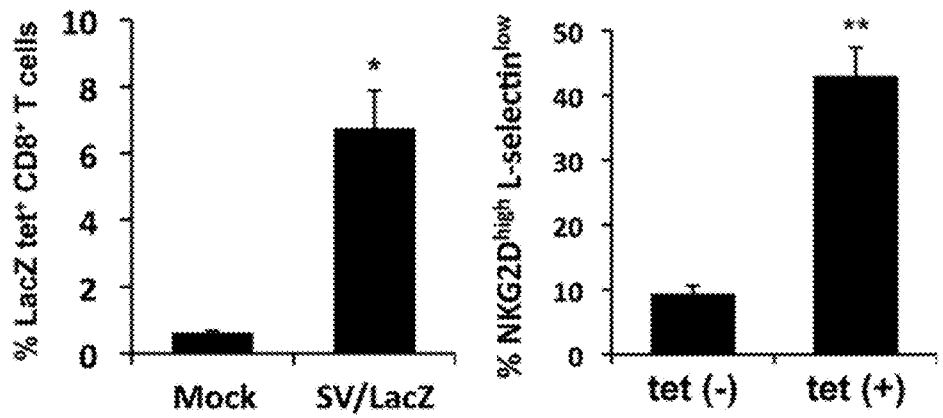
Figure 5A:
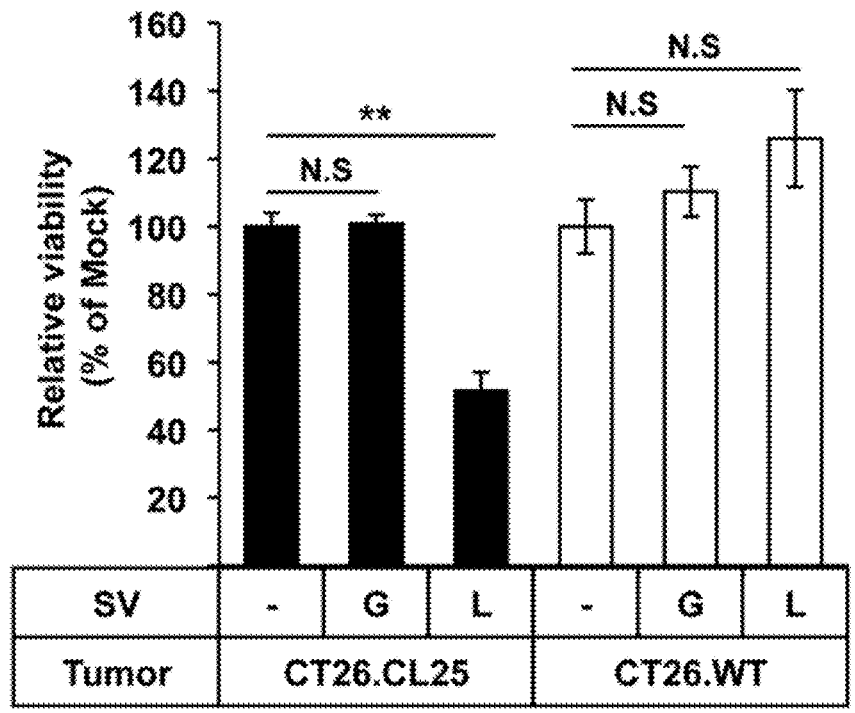
FIGS. 5a and 5b. Lymphocytes acquire LacZ-specific cytotoxicity during SV/LacZ therapy. Lung lymphocytes were extracted from CT26.CL25.Fluc lung tumor-bearing mice 7 days after Mock (−), SV/GFP (G) or SV/LacZ (L) treatment started. Extracted lung lymphocytes were co-cultured with CT26.CL25.Fluc cells (CT26.CL25) or CT26.WT.Fluc cells (CT26.WT) for 2 days to determine (a) the cytotoxicity of lung lymphocytes against each tumor cell population, and (b) IFN-γ secretion from the lung lymphocytes in response to co-culture with each tumor cell population, as described in Materials and Methods (data in (a) and (b) are expressed as mean±SD, N=3). **$p<0.01$ (significantly different from Mock). N.D, not detected. SV, Sindbis viral vector.
Figure 5B:
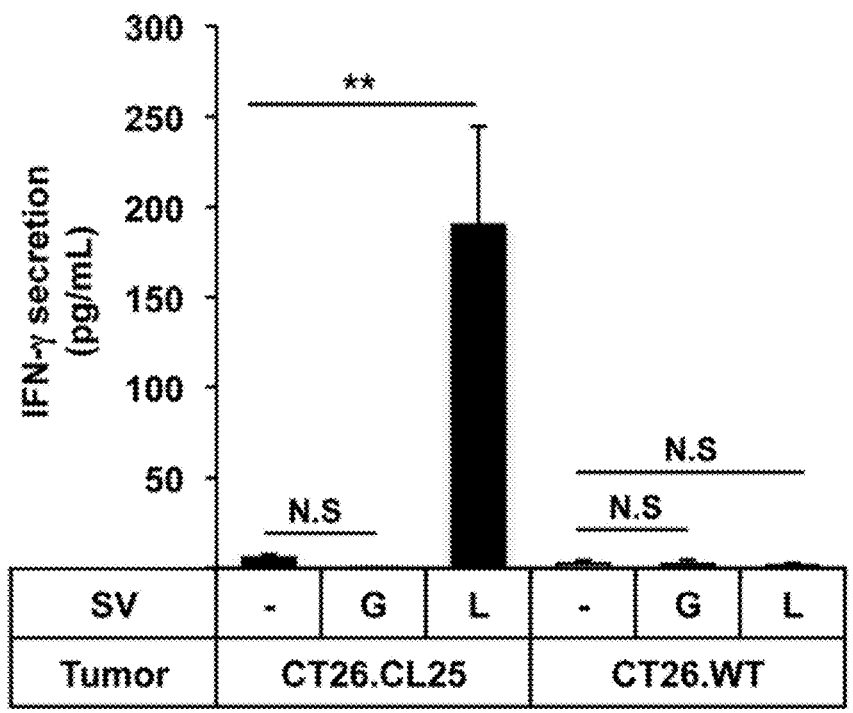

Example 5: SV/LacZ Treatment Induces Lymphocyte Cytotoxicity Against CT26.CL25 Tumor Cells As shown in FIG. 4d, LacZ-specific CD8+ T cells in the lungs of lung tumor-bearing mice treated with SV/LacZ appeared to be activated. In order to investigate the function of these cells, an ex vivo cytotoxicity assay was performed using lung lymphocytes obtained from lung tumor (CT26.CL25)-bearing mice receiving SV/LacZ (or SV/GFP) therapy. As shown in FIG. 5a, the viability of CT26.CL25 tumor cells was significantly lower when they were co-cultured with lung lymphocytes from SV/LacZ-treated mice compared to when they were co-cultured with lymphocytes from mock or SV/GFP-treated mice. Notably, lung lymphocytes from SV/LacZ-treated mice did not affect the viability of LacZ-negative CT26.WT tumor cells, demonstrating the antigen-specific nature of the immune response in the lung. Consistent with this result, only lung lymphocytes from SV/LacZ-treated mice that were co-cultured with LacZ-expressing CT26.CL25 tumor cells showed an increase in IFN-γ production (FIG. 5b).

Figure 6A:
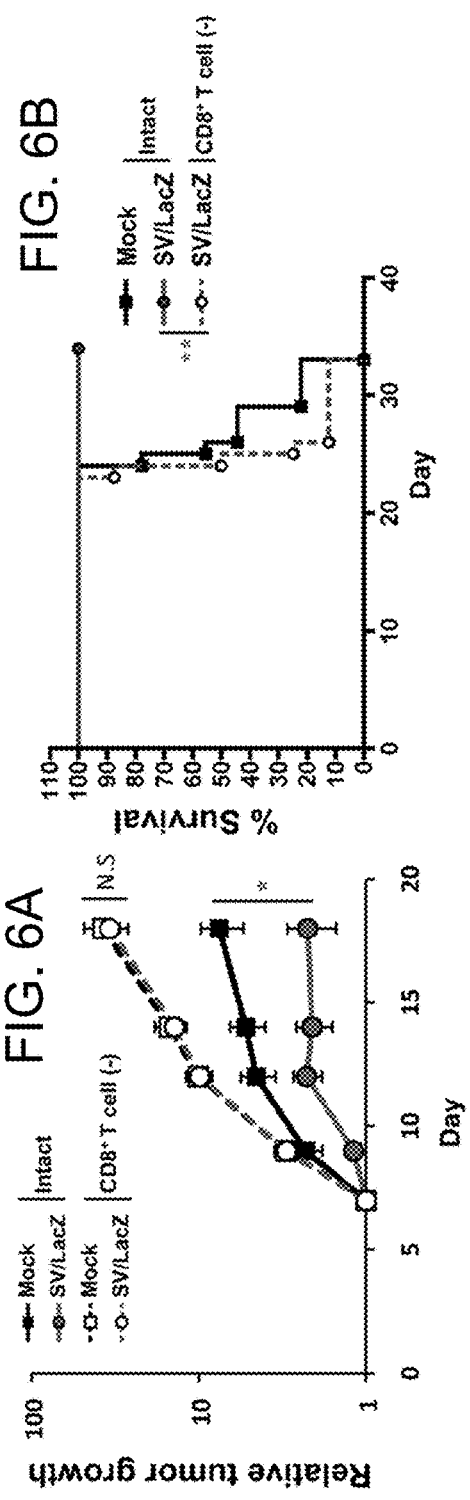
FIGS. 6a-6c. CD8$^+$ T cells are required for the enhanced therapeutic effect of SV/LacZ. The therapeutic effect of SV/LacZ was compared between intact and CD8$^+$ T cell-depleted (CD8$^+$ T cell (−)) mice in the (a) s.c., (b) i.p., and (c) lung tumor models. (a) The size of CT26.CL25 s.c. tumors at indicated time points was measured and plotted for each group (N=5). (b) Survival rates in CT26.CL25 i.p. tumor-bearing mice were monitored and plotted as Kaplan-Meier survival plots. N=8-9 (c) Tumor growth (left panel) and survival rates (right panel) in CT26.CL25.Fluc lung tumor-bearing mice were analyzed. Relative tumor growth was quantified as in FIG. 1c, and survival rates are shown as Kaplan-Meier survival plots (N=5). Data in (a) and (c) are expressed as mean±SEM. *$P<0.05$, **$P<0.01$. N.S, not significant; SV, Sindbis viral vector.
Figure 6B:
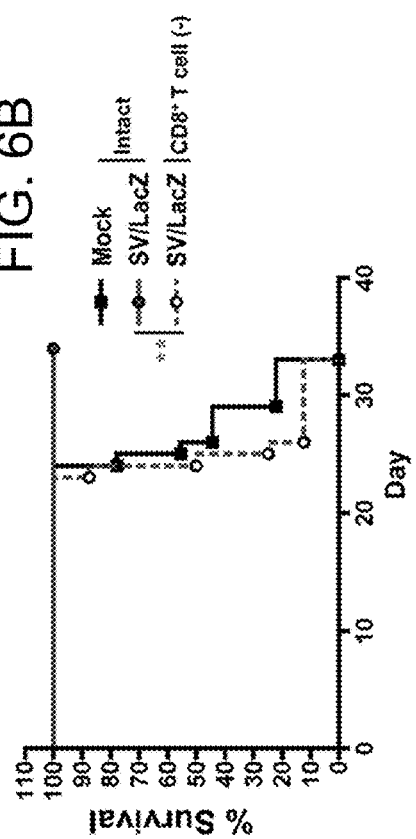

Example 6: CD8+ T Cells are Required for the Antigen-Specific Enhanced Therapeutic Effect of SV/LacZ The results of the cytotoxicity and IFN-γ secretion assays (FIG. 5) are consistent with the in vivo observation that SV/LacZ has a significantly stronger therapeutic effect against CT26.CL25 tumors than control vectors (FIG. 1), and with the observation that SV/LacZ induces a powerful LacZ-specific CD8+ T cell response in tumor-bearing mice (FIG. 4). Taken together, these results strongly suggest the involvement of CD8+ T cells in the antigen-specific benefits of SV/TAA therapy. In order to directly determine the role of CD8+ T cells in the therapeutic effects observed, the CD8+ T cell population in mice bearing s.c. (FIG. 6a), peritoneal (FIG. 6b), and lung (FIG. 6c) tumors was depleted, and confirmed that in the absence of CD8+ T cells, the therapeutic efficacy of SV/LacZ was greatly reduced in all 3 models.

Example 7: SV/LacZ Therapy Induces Epitope Spreading

Figure 7A:
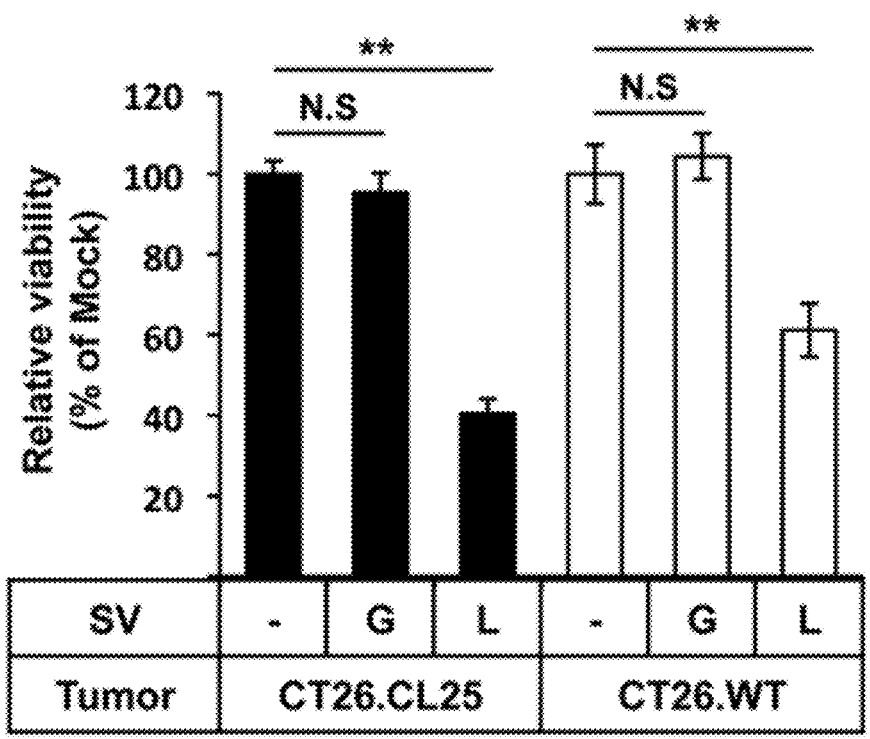
FIGS. 7a-7e. Immunity against endogenous CT26 TAM develops during SV/LacZ therapy. (a,b) Splenocytes were extracted from CT26.CL25.Fluc lung tumor-bearing mice at 7 days after Mock (−), SV/GFP (G) or SV/LacZ (L) treatment started. Extracted splenocytes were co-cultured with CT26.CL25.Fluc (CT26.CL25) or CT26.WT.Fluc (CT26.WT) cells for 2 days to determine (a) the cytotoxicity of the splenocytes towards each tumor cell population, and (b) IFN-γ secretion from the splenocytes in response to co-culture with each tumor cell population, as described in Materials and Methods (mean±SD, N=3). (c) CT26. WT.Fluc tumor was inoculated i.v. into naïve and CT26.CL25 SV/LacZ-treated tumor-cured mice at more than 60 days after the last SV/LacZ treatment, and tumor growth in the lung was analyzed at the indicated time points by bioluminescent imaging. The left panel shows representative IVIS images of 2 independent experiments. The right panel shows the quantification of tumor bioluminescence at the indicated time points (mean±SEM, N=8). (d) CT26.WT.Fluc tumors were inoculated i.v. into naïve (N) and SV/LacZ-treated tumor-cured mice (S) at more than 30 days after the last SV/LacZ treatment. 8 days after tumor inoculation, splenocytes were extracted from each mouse and incubated with LacZ, gp70, or control peptides for 3 days. After the incubation, LacZ- or gp70-specific induction of IFN-γ secretion was analyzed as described in Materials and Methods (mean±SEM, N=3). (e) The number of gp70-specific CD8$^+$ T cells in splenocytes extracted in (d) was quantified by flow cytometry using gp70 tetramers (mean±SD, N=3). *$p<0.05$, **$p<0.01$ (significantly different from Mock or Naïve). N.D, not detected; SV, Sindbis viral vector.
Figure 7B:
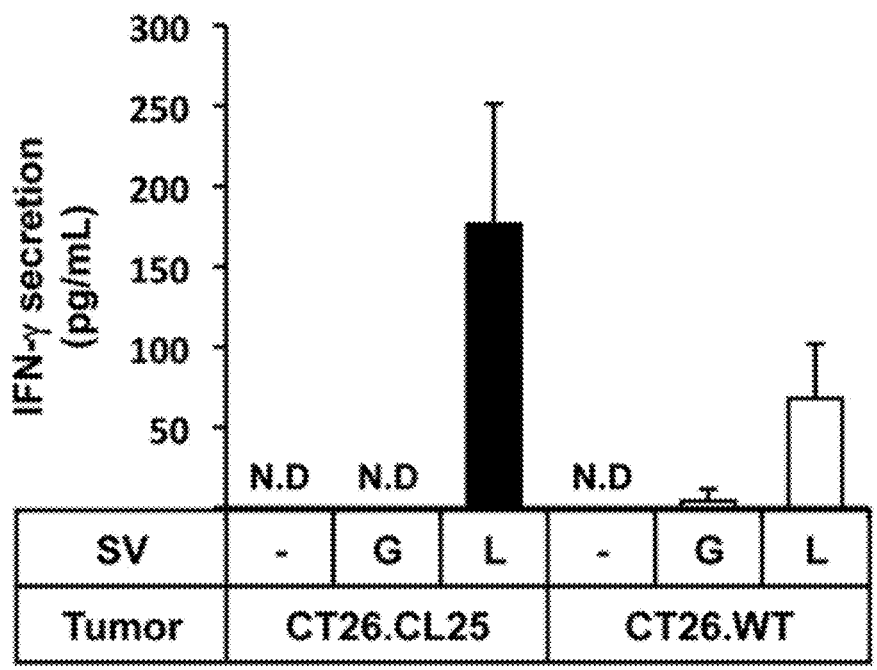
Figure 7C:
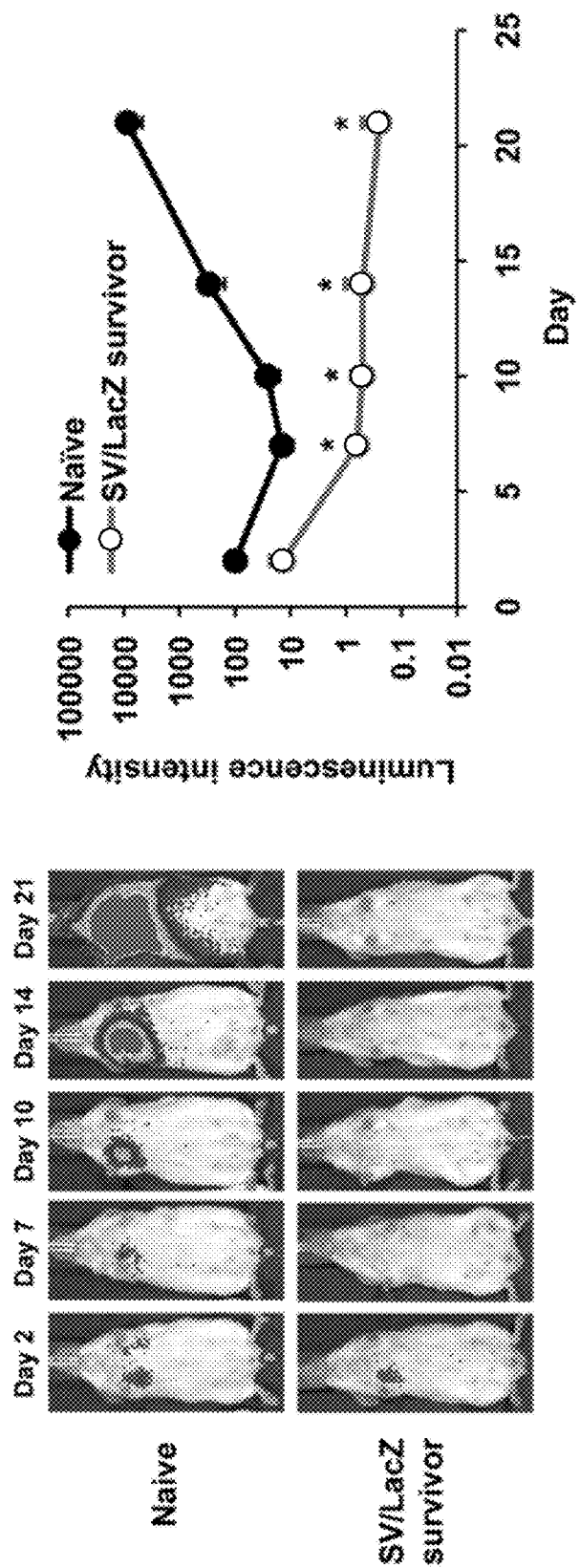
Figure 7D:
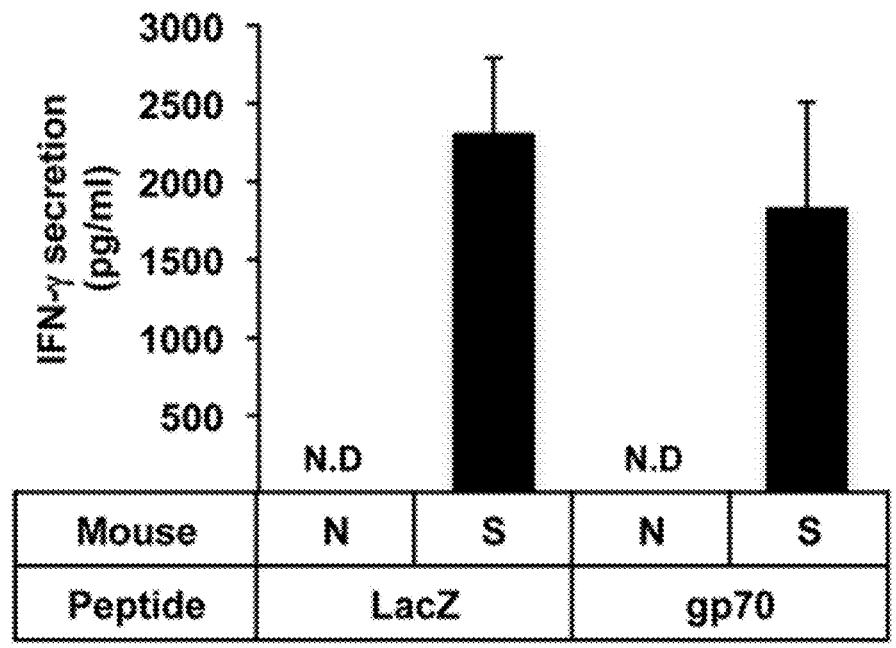
Figure 7E:
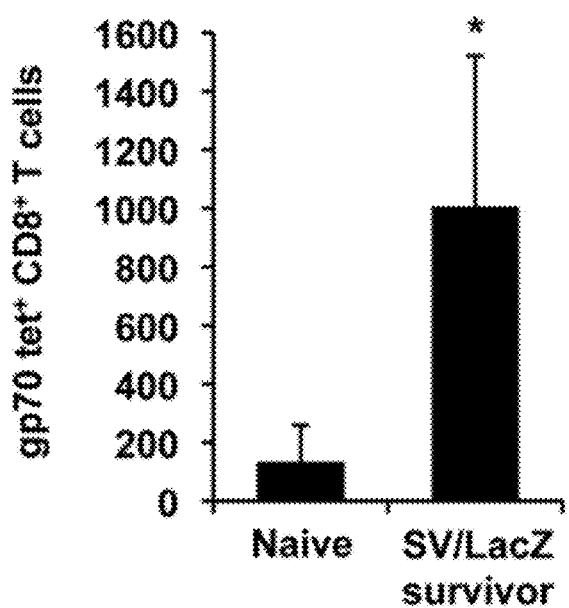
Figure 8:
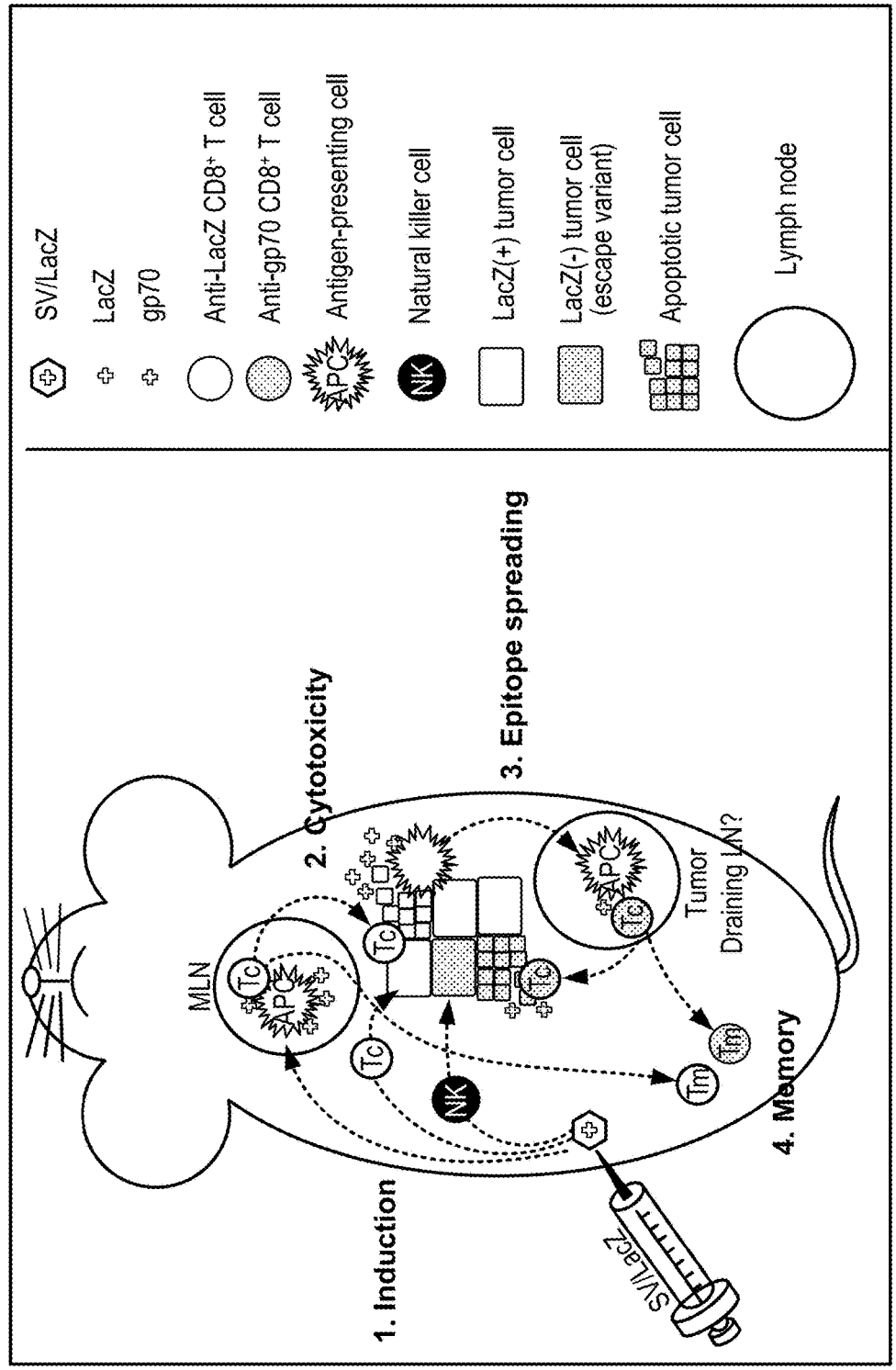
FIG. 8. Four-step model for the activation of CD8+ T cells during SV/TAA therapy. Step 1: i.p. injection of SV/LacZ results in transient immunogenic expression of LacZ in the mediastinal lymph nodes (dark blue arrow), followed by the induction of T cell activation at this site and/or in alternative locations (light blue arrow). NK cells are also activated against the tumor cells (brown arrow). Step 2 (red arrow): LacZ-specific CD8+ T cell cytotoxicity results in the destruction of tumor cells and the subsequent release of tumor associated antigens such as LacZ and gp70. Step 3 (green arrows): Antigen-presenting cells capture and present these antigens to CD8+ T cells in the tumor-draining lymph nodes, resulting in epitope spreading, including the induction of gp70-specific CD8+ T cells that can potentially target LacZ(−) tumor cell escape variants. Step 4 (purple arrows): memory CD8+ T cells against a variety of tumor-associated antigens are generated. APC, antigen-presenting cell; LN, lymph node; MLN, mediastinal lymph node; NK, Natural killer cell; SV, Sindbis viral vector; TAA, tumor-associated antigen; Tc, cytotoxic CD8+ T cell; Tm, memory CD8+ T cell.

Surprisingly, it was found that, unlike lung lymphocytes, splenocytes from SV/LacZ-treated tumor-cured mice acquired cytotoxicity against not only CT26.CL25 cells, but also LacZ-negative CT26.WT cells (FIG. 7a). Consistently, an increase in IFN-γ production was observed when these splenocytes were co-cultured with CT26.WT cells, although the extent of the production was lower than when they were co-cultured with CT26.CL25 cells (FIG. 7b). Based on these results, it was hypothesized that SV/LacZ-treated tumor-cured mice might have acquired resistance to LacZ-negative CT26.WT tumors. To determine if this was the case, CT26.WT cells were injected i.v. (FIG. 7c) or i.p. (data not shown) into SV/LacZ-treated tumor-cured mice, and found that the tumors did not grow. In contrast, tumor growth was readily observed in control (naïve) mice. These results suggest that an immune response to endogenous CT26 tumor antigens might have developed as a consequence of SV/LacZ therapy, a concept known alternatively as epitope spreading, antigen spreading, determinant spreading, or antigen cascade [32]. To confirm that epitope spreading occurred during SV/LacZ therapy, gp70 was focused on, which is an endogenous CT26 TAA. As shown in FIG. 7d, an increase in IFN-γ secretion from splenocytes taken from SV/LacZ-treated tumor-cured mice was observed after culturing these cells with either gp70 or LacZ peptides, whereas, neither peptide induced IFN-γ secretion from naïve splenocytes. These results indicate that splenocytes from SV/LacZ-treated tumor-cured mice could respond to endogenous CT26 TAAs such as gp70 in addition to LacZ. Consistent with this observation, flow cytometry analysis using gp70 tetramers demonstrated that the number of gp70-specific CD8+ T cells was increased in the spleens of SV/LacZ-treated tumor-cured mice compared with naïve mice (FIG. 7e). Taken together, these results indicate that SV/LacZ therapy against CT26.CL25 tumors induced epitope spreading, which led to the development of immunity against other antigen(s) expressed on the CT26 tumors.

Disclosed herein, a mouse cancer-TAA system was used to investigate the use of SV vectors carrying TAAs for cancer therapy, and the following key observations were made: (i) SV represents a potentially powerful therapeutic platform for the immunogenic delivery of TAAs, (ii) the therapeutic benefit obtained from SV/TAA does not necessarily require the direct targeting of tumor cells, (iii) SV/TAA therapy involves transient early delivery of the TAA to lymph nodes draining the injection site, in particular the MLN in the case of i.p. SV injection, (iv) SV/TAA therapy induces a potent TAA-specific $CD8^+$ T cell response, that is subsequently redirected against tumor cells expressing the cognate TAA, (v) SV/TAA therapy leads to epitope spreading, providing a possible solution to the problem of tumor escape by TAA loss or modification, and (vi) SV/TAA therapy ultimately leads to long-term survival of tumor-bearing mice, and to the generation of long-lasting memory $CD8^+$ T cells against multiple TAAs.

Based on these findings, a four-step model for the activation of CD8+ T cell mediated anti-tumor immunity during SV/TAA therapy (induction, cytotoxicity, epitope spreading, and memory), is provided.

Over the last few decades, a variety of methods have been developed for the immunogenic delivery of TAAs, including the employment of vectors that target Antigen Presenting Cells (APCs) [33], or are directly injected into lymph nodes [34]. Disclosed herein, it was demonstrated that a single i.p. injection of SV/TAA leads to the rapid immunogenic delivery of TAAs to the MLN. TAA expression in the MLN is transient, and likely would have remained unnoticed without the use of the sensitive IVIS imaging system. I.p. injections are frequently used in animal studies, and are becoming increasingly common in the clinic [35]. Observations of transient TAA expression and subsequent T cell activation at this site (FIG. 2) may therefore have broad implications for the development of cancer immunotherapies. In this context, Hsu et al. have recently demonstrated that i.p.-injected cytomegalovirus resulted in the productive infection of $CD169^+$ macrophages in the MLN [28]. Consistent with this, depletion of macrophages substantially reduced the expression of SV-derived heterologous protein in the MLN (unpublished results). Notably, however, the induction of anti-TAA $CD8^+$ T cell immunity was not significantly inhibited in macrophage-depleted mice that were treated with SV/LacZ (unpublished results). This discrepancy may be resolved by the observation that while both macrophages and dendritic cells (DC) express viral antigens in draining lymph nodes, only DC efficiently present these antigens to naïve $CD8^+$ T cells [36]. Another possible explanation is the fact that additional lymph nodes besides the MLN drain the peritoneal cavity. Indeed, transient heterologous protein expression was also observed in the abdominal cavity of SV-treated mice (FIG. 10, top panel). Further studies are needed, and are underway, to clarify the role of TAA delivery to the MLN during SV/TAA therapy.

Figure 6C:
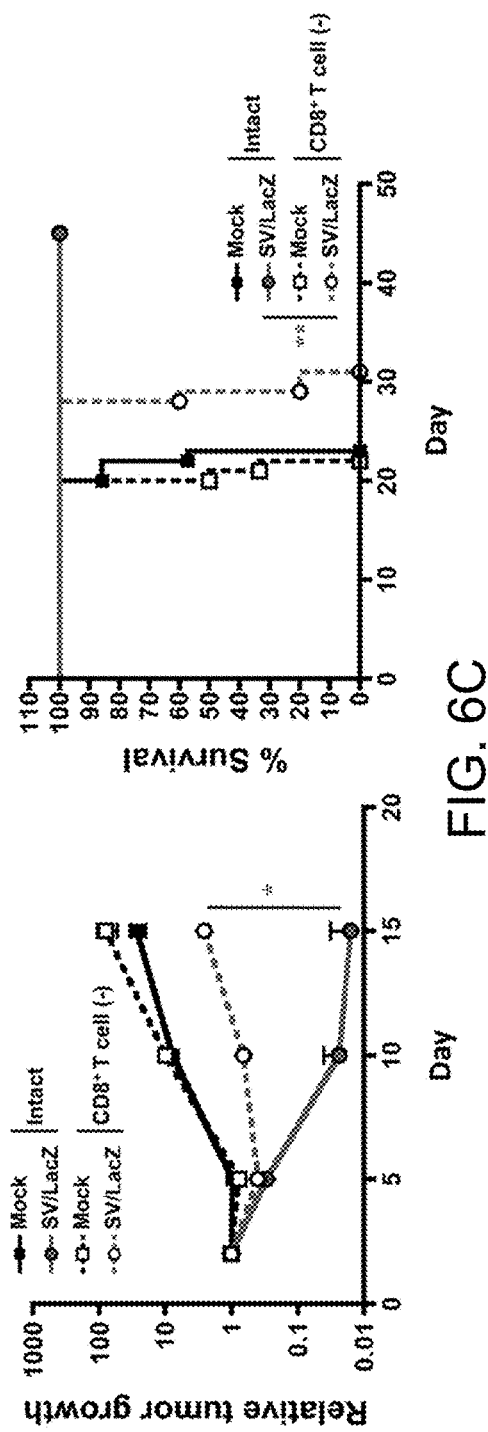
Figure 13A:
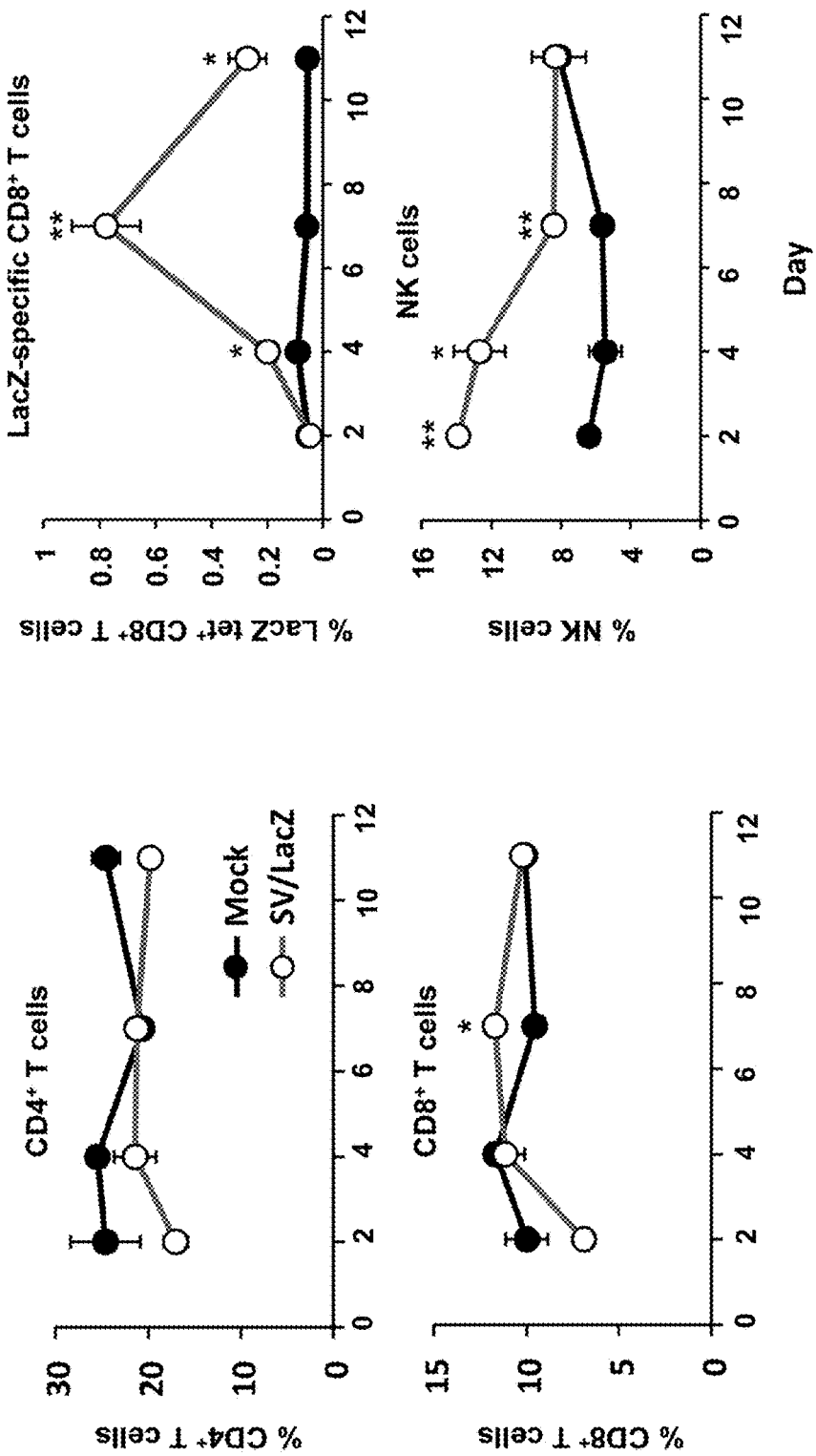
FIGS. 13a and 13b. NK cells are activated at an early stage of SV therapy. (a) Percentages of lung CD4+ T cells, CD8+ T cells, LacZ-specific CD8+ T cells, and NK (CD3−CD122+) cells within the total lung immune cell (CD45+) population from CT26.CL25.Fluc lung tumor-bearing mice were analyzed at indicated time points after Mock or SV/LacZ treatment started. (b) Expression of NKG2D on NK cells in the lung from CT26.CL25.Fluc lung tumor-bearing mice was analyzed at indicated time points after mock or SV/LacZ treatment started. Data are expressed as mean±SEM (N=3). *p<0.05, **p<0.01. LacZ, β-galactosidase; NK, natural killer cell; SV, Sindbis viral vector; tet, tetramer.
Figure 13B:
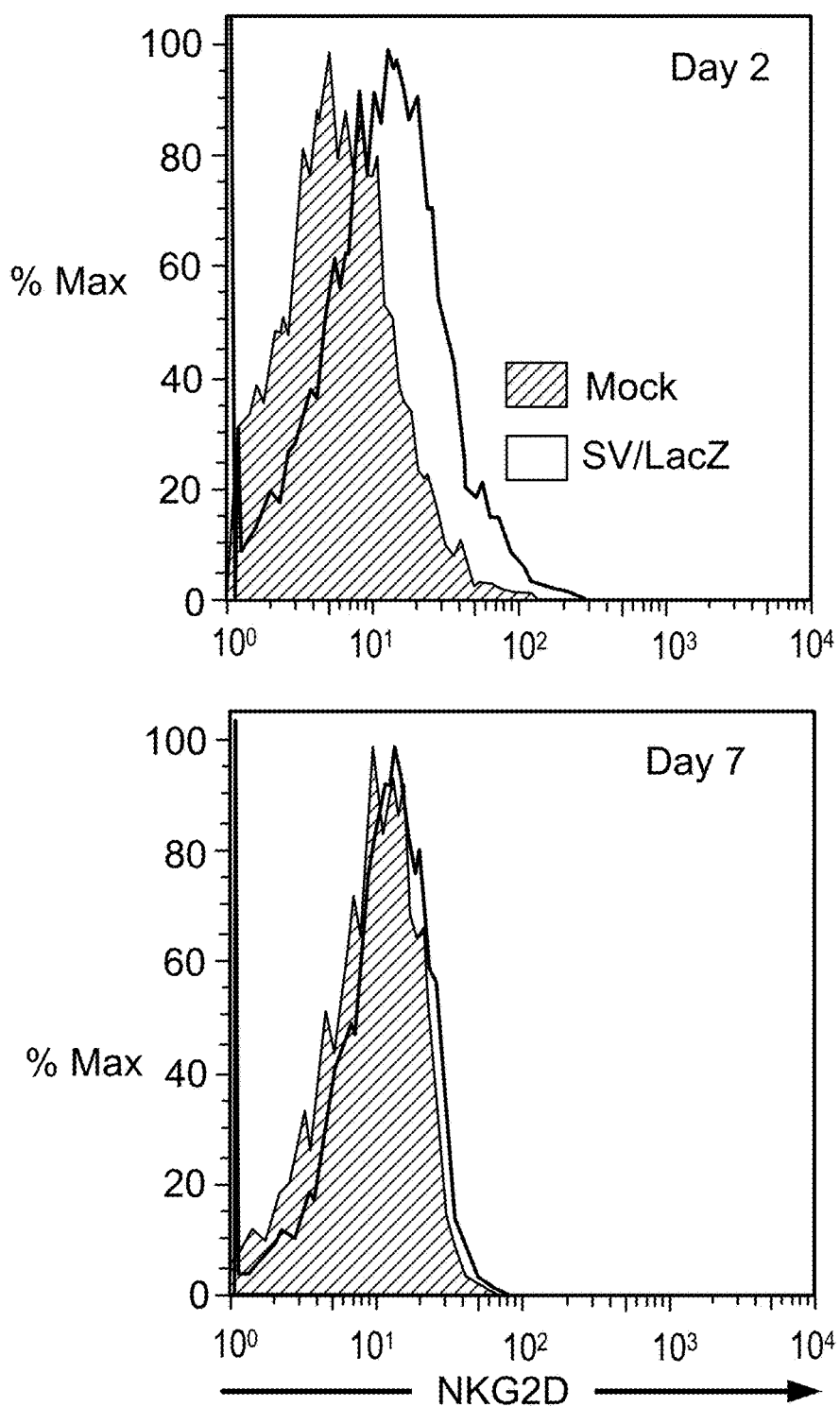

Besides the activation of T cells in the MLN, there appears to be a systemic redistribution of $CD8^+$ T cells early after SV/TAA injection. Various tissues, including the peritoneum (FIG. 11a) and the lung (FIG. 13), show a reduction in $CD8^+$ T cells in the first 1-2 days after SV/TAA injection. The apparent efflux of T cells from these tissues coincides with their influx into the MLN (FIG. 2B). It is interesting to note that during this early phase, lung tumors in SV/TAA-treated mice already appear to shrink (FIG. 1c). Moreover, this early therapeutic effect was also observed in mice treated with control vectors that do not express the TAA (FIG. 1c), in SV-treated mice bearing tumors that do not express the TAA (FIG. 9), and in SV/TAA-treated mice that were depleted of $CD8^+$ T cells (FIG. 6c). One possible explanation for this is the activation of natural killer (NK) cells by SV. It has been previously shown that SV therapy induces a robust NK cell response in tumor-bearing mice [19]. In the CT26 lung model, a rapid influx of NKG2D-expressing NK cells into the lung was observed as early as 2 days after SV injection, several days before the maximum influx of TAA-specific $CD8^+$ T cells (FIG. 13).

One of the limitations of cancer vaccine strategies is that the inherent heterogeneity and genomic instability of tumor cell populations, coupled with the selective pressure induced by the treatment, can lead to tumor evasion by loss or modification of the TAA used in the vaccine [38, 39]. In this context, an interesting and therapeutically significant observation is the induction of epitope spreading, i.e. the expansion of the anti-tumor T cell response to incorporate novel TAAs that are endogenous to the tumor, but not delivered by the vector [32] during SV/TAA therapy (FIG. 7). Clinical trials are increasingly incorporating the analysis of epitope spreading [40], and in some cases a positive correlation between the induction of epitope spreading and therapeutic efficacy has been shown [25]. These developments may signify a paradigm shift in the design of cancer vaccines, whereby an emphasis would be placed on the induction of a strong diversified T cell response that could potentially be effective even against tumors with heterogeneous antigen expression.

In summary, the present application provides methods for the use of SV/TAA for cancer therapy, and provides valuable insight into the mechanisms underlying SV/TAA efficacy. Pursuant to the present invention, using SV vectors that carry a TAA not only greatly enhances SV efficacy, but also abrogates the need for tumor cell targeting—a hitherto prerequisite for effective oncolytic SV therapy—thereby paving the way for a much broader application of SV anti-cancer therapy. The current findings, in addition to previous investigations into the oncolytic potential of SV [15, 16], compliment and expand upon earlier studies on the use of SV nucleic acid [41] and replicon particle [42] vaccines, and illustrate the versatility of SV anti-cancer therapy.

REFERENCES

1. Russell, S J, Peng, K W, and Bell, J C. Oncolytic virotherapy. *Nat Biotechnol* 30: 658-670.
2. Liu, T C, Galanis, E, and Kirn, D (2007). Clinical trial results with oncolytic virotherapy: a century of promise, a decade of progress. *Nat Clin Pract Oncol* 4: 101-117.
3. Wein, L M, Wu, J T, and Kirn, D H (2003). Validation and analysis of a mathematical model of a replication-competent oncolytic virus for cancer treatment: implications for virus design and delivery. *Cancer Res* 63: 1317-1324.
4. Vaha-Koskela, M J, et al. Resistance to two heterologous neurotropic oncolytic viruses, Semliki Forest virus and vaccinia virus, in experimental glioma. *J Virol* 87: 2363-2366.
5. Vaha-Koskela, M J, Heikkila, J E, and Hinkkanen, A E (2007). Oncolytic viruses in cancer therapy. *Cancer Lett* 254: 178-216.
6. Wildner, O, Blaese, R M, and Morris, J C (1999). Therapy of colon cancer with oncolytic adenovirus is enhanced by the addition of herpes simplex virus-thymidine kinase. *Cancer Res* 59: 410-413.
7. Hermiston, T W, and Kuhn, I (2002). Armed therapeutic viruses: strategies and challenges to arming oncolytic viruses with therapeutic genes. *Cancer Gene Ther* 9: 1022-1035.

8. Prestwich, R J, et al. (2009). The case of oncolytic viruses versus the immune system: waiting on the judgment of Solomon. *Hum Gene Ther* 20: 1119-1132.
9. Kawakami, Y, et al. (1994). Cloning of the gene coding for a shared human melanoma antigen recognized by autologous T cells infiltrating into tumor. *Proc Natl Acad Sci USA* 91: 3515-3519.
10. Lee, P P, et al. (1999). Characterization of circulating T cells specific for tumor-associated antigens in melanoma patients. *Nat Med* 5: 677-685.
11. Cheever, M A, et al. (2009). The prioritization of cancer antigens: a national cancer institute pilot project for the acceleration of translational research. *Clin Cancer Res* 15: 5323-5337.
12. Diaz, R M, et al. (2007). Oncolytic immunovirotherapy for melanoma using vesicular stomatitis virus. *Cancer Res* 67: 2840-2848.
13. Fourcade, J, et al. CD8(+) T cells specific for tumor antigens can be rendered dysfunctional by the tumor microenvironment through upregulation of the inhibitory receptors BTLA and PD-1. *Cancer Res* 72: 887-896.
14. Strauss, J H, and Strauss, E G (1994). The alphaviruses: gene expression, replication, and evolution. *Microbiol Rev* 58: 491-562.
15. Tseng, J C, Levin, B, Hirano, T, Yee, H, Pampeno, C, and Meruelo, D (2002). In vivo antitumor activity of Sindbis viral vectors. *J Natl Cancer Inst* 94: 1790-1802.
16. Tseng, J C, et al. (2004). Systemic tumor targeting and killing by Sindbis viral vectors. *Nat Biotechnol* 22: 70-77.
17. Tsuji, M, et al. (1998). Recombinant Sindbis viruses expressing a cytotoxic T-lymphocyte epitope of a malaria parasite or of influenza virus elicit protection against the corresponding pathogen in mice. *J Virol* 72: 6907-6910.
18. Tseng, J C, et al. (2004). Using sindbis viral vectors for specific detection and suppression of advanced ovarian cancer in animal models. *Cancer Res* 64: 6684-6692.
19. Granot, T, Venticinque, L, Tseng, J C, and Meruelo, D. Activation of cytotoxic and regulatory functions of NK cells by Sindbis viral vectors. *PLoS One* 6: e20598.
20. Huang, P Y, Guo, J H, and Hwang, L H. Oncolytic Sindbis virus targets tumors defective in the interferon response and induces significant bystander antitumor immunity in vivo. *Mol Ther* 20: 298-305.
21. Bredenbeek, P J, Frolov, I, Rice, C M, and Schlesinger, S (1993). Sindbis virus expression vectors: packaging of RNA replicons by using defective helper RNAs. *J Virol* 67: 6439-6446.
22. Alexopoulou, L, Holt, A C, Medzhitov, R, and Flavell, R A (2001). Recognition of double-stranded RNA and activation of N F-kappaB by Toll-like receptor 3. *Nature* 413: 732-738.
23. Leitner, W W, et al. (2003). Alphavirus-based DNA vaccine breaks immunological tolerance by activating innate antiviral pathways. *Nat Med* 9: 33-39.
24. Doyle, T C, Burns, S M, and Contag, C H (2004). In vivo bioluminescence imaging for integrated studies of infection. *Cell Microbiol* 6: 303-317.
25. Corbiere, V, et al. Antigen spreading contributes to MAGE vaccination-induced regression of melanoma metastases. *Cancer Res* 71: 1253-1262.
26. Lopes Cardozo, A M, et al. (2001). Metastatic pattern of CC531 colon carcinoma cells in the abdominal cavity: an experimental model of peritoneal carcinomatosis in rats. *Eur J Surg Oncol* 27: 359-363.
27. Tilney, N L (1971). Patterns of lymphatic drainage in the adult laboratory rat. *J Anat* 109: 369-383.
28. Hsu, K M, Pratt, J R, Akers, W J, Achilefu, S I, and Yokoyama, W M (2009). Murine cytomegalovirus displays selective infection of cells within hours after systemic administration. *J Gen Virol* 90: 33-43.
29. Geissmann, F, Jung, S, and Littman, D R (2003). Blood monocytes consist of two principal subsets with distinct migratory properties. *Immunity* 19: 71-82.
30. Diefenbach, A, Jamieson, A M, Liu, S D, Shastri, N, and Raulet, D H (2000). Ligands for the murine NKG2D receptor: expression by tumor cells and activation of NK cells and macrophages. *Nat Immunol* 1: 119-126.
31. Arbones, M L, et al. (1994). Lymphocyte homing and leukocyte rolling and migration are impaired in L-selectin-deficient mice. *Immunity* 1: 247-260.
32. Vanderlugt, C L, and Miller, S D (2002). Epitope spreading in immune-mediated diseases: implications for immunotherapy. *Nat Rev Immunol* 2: 85-95.
33. Gardner, J P, et al. (2000). Infection of human dendritic cells by a sindbis virus replicon vector is determined by a single amino acid substitution in the E2 glycoprotein. *J Virol* 74: 11849-11857.
34. Kreiter, S, et al. Intranodal vaccination with naked antigen-encoding RNA elicits potent prophylactic and therapeutic antitumoral immunity. *Cancer Res* 70: 9031-9040.
35. Galanis, E, et al. Phase I trial of intraperitoneal administration of an oncolytic measles virus strain engineered to express carcinoembryonic antigen for recurrent ovarian cancer. *Cancer Res* 70: 875-882.
36. Norbury, C C, Malide, D, Gibbs, J S, Bennink, J R, and Yewdell, J W (2002). Visualizing priming of virus-specific CD8+ T cells by infected dendritic cells in vivo. *Nat Immunol* 3: 265-271.
37. Duwe, B V, Sterman, D H, and Musani, A I (2005). Tumors of the mediastinum. *Chest* 128: 2893-2909.
38. Khong, H T, and Restifo, N P (2002). Natural selection of tumor variants in the generation of "tumor escape" phenotypes. *Nat Immunol* 3: 999-1005.
39. Vergati, M, Intrivici, C, Huen, N Y, Schlom, J, and Tsang, K Y. Strategies for cancer vaccine development. *J Biomed Biotechnol* 2010.
40. Carmichael, M G, et al. Results of the first phase 1 clinical trial of the HER-2/neu peptide (GP2) vaccine in disease-free breast cancer patients: United States Military Cancer Institute Clinical Trials Group Study I-04. *Cancer* 116: 292-301.
41. Leitner, W W, Ying, H, Driver, D A, Dubensky, T W, and Restifo, N P (2000). Enhancement of tumor-specific immune response with plasmid DNA replicon vectors. *Cancer Res* 60: 51-55.
42. Cheng, W F, et al. (2002). Cancer immunotherapy using Sindbis virus replicon particles encoding a VP22-antigen fusion. *Hum Gene Ther* 13: 553-568.
43. Gavin, M A, Gilbert, M J, Riddell, S R, Greenberg, P D, and Bevan, M J (1993). Alkali hydrolysis of recombinant proteins allows for the rapid identification of class I MHC-restricted CTL epitopes. *J Immunol* 151: 3971-3980.
44. Huang, A Y, et al. (1996). The immunodominant major histocompatibility complex class I-restricted antigen of a murine colon tumor derives from an endogenous retroviral gene product. *Proc Natl Acad Sci USA* 93: 9730-9735.
45. Restifo, N P, et al. (1995). Antigen processing in vivo and the elicitation of primary CTL responses. *J Immunol* 154: 4414-4422.

The present invention is not to be limited in scope by the specific embodiments described herein. Indeed, various modifications of the invention in addition to those described herein will be apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes

---

---

What is claimed is:

1. A method for treating a mammal having a tumor, the method comprising:
   identifying at least one tumor associated antigen (TAA) expressed by the tumor,
   administering by intravenous or intraperitoneal injection to the mammal harboring said tumor an effective amount of a replication defective Sindbis viral vector comprising a gene encoding said TAA,
   wherein expression of said TAA induces a TAA-specific T cell immune response in the lymph nodes that drain the site of vector administration followed by generation and influx of effector and memory TAA-specific CD8+ T cells into the tumor site, and wherein effector and memory TAA-specific CD8+ T cells display cytotoxicity against TAA positive and negative tumor cells.

2. The method of claim 1, wherein said tumor is selected from the group consisting of subcutaneous, intraperitoneal, and lung cancer tumor.

3. The method of claim 1, wherein said vector introduces the TAA in the lymph nodes prior to the activation of a TAA-specific immune response by antigen presenting cells (APC) in the mammal.

4. The method of claim 1, wherein the immune response induced in the draining lymph nodes of the mammal further induces an adaptive anti-tumor immune response comprising activation of TAA-specific CD4+ T cells, NK cells, macrophages, monocytes, dendritic cells and neutrophils in the mammal.

5. The method of claim 1, wherein the mammal is a human.

6. The method of claim 1, wherein said tumor is a solid tumor.

7. The method of claim 1, wherein the Sindbis viral vector is administered in combination with chemotherapy.

8. The method of claim 6, wherein the solid tumor is an ovarian cancer tumor.

9. The method of claim 8, wherein the TAA is New York-ESO-1 (NY-ESO-1).

10. The method of claim 8, wherein the TAA is carcinoembryonic antigen (CEA).

* * * * *

UNITED STATES PATENT AND TRADEMARK OFFICE
CERTIFICATE OF CORRECTION

PATENT NO. : 10,010,628 B2
APPLICATION NO. : 14/478783
DATED : July 3, 2018
INVENTOR(S) : Daniel Meruelo, Tomer Granot and Yoshihide Yamanashi It is certified that error appears in the above-identified patent and that said Letters Patent is hereby corrected as shown below:

In the Specification

Column 1, Line 12, please delete:
"The United States Government has certain rights to this invention by virtue of funding received from the U.S. Public Health grants CA100687 from the National Cancer Institute, National Institutes of Health and Departments of Health and Human Services."

And insert therefor:
-- GOVERNMENT CLAUSE
This invention was made with government support under CA100687 awarded by the National Institutes of Health and the Departments of Health and Human Services. The government has certain rights in the invention. --

Signed and Sealed this
Twenty-first Day of August, 2018

Andrei Iancu
*Director of the United States Patent and Trademark Office*

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Pro His Pro Ala Arg Ile Gly Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Pro Ser Tyr Val Tyr His Gln Phe
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Pro Tyr Leu Gly Trp Leu Val Phe
1               5
```